(12) United States Patent
Christensen

(10) Patent No.: US 7,686,848 B2
(45) Date of Patent: *Mar. 30, 2010

(54) PROSTHETIC FOOT WITH ENERGY TRANSFER

(75) Inventor: Roland J. Christensen, Gunnison, UT (US)

(73) Assignee: Freedom Innovations, LLC, Irvine, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/006,801

(22) Filed: Jan. 4, 2008

(65) Prior Publication Data

US 2008/0183301 A1      Jul. 31, 2008

Related U.S. Application Data

(63) Continuation-in-part of application No. 11/377,228, filed on Mar. 15, 2006, now Pat. No. 7,572,299, which is a continuation-in-part of application No. 11/098, 828, filed on Apr. 4, 2005, now Pat. No. 7,341,603, which is a continuation-in-part of application No. 10/738,645, filed on Dec. 16, 2003, now Pat. No. 6,875,242, which is a continuation-in-part of application No. 10/137,933, filed on May 3, 2002, now Pat. No. 6,663,673, which is a continuation-in-part of application No. 09/607,494, filed on Jun. 30, 2000, now abandoned.

(51) Int. Cl.
*A61F 2/66* (2006.01)
(52) U.S. Cl. .......................................... 623/56; 623/52
(58) Field of Classification Search .............. 623/47–56
See application file for complete search history.

(56) References Cited

U.S. PATENT DOCUMENTS 42,799 A    5/1864   Shepard (Continued)

FOREIGN PATENT DOCUMENTS

BR        9304552        7/1995

(Continued)

OTHER PUBLICATIONS www.micacorp.com/products/genesis2/, MICA Manufacturing Corporation, Genesis II Prosthetic Foot, Nov. 24, 2004, 1 page.

(Continued)

*Primary Examiner*—Bruce E Snow
(74) *Attorney, Agent, or Firm*—Thorpe North & Western LLP

(57) ABSTRACT

A prosthetic foot device with variable stiffness response includes a variable energy transfer mechanism disposed between first and second foot members to transfer a variable amount of energy between the members during use. A chamber is associated with one of the first and second foot members, and a piston is associated with another of the first and second foot members and is movable in the chamber. At least one aperture is formed between the piston and the chamber. A variable viscosity fluid is disposed in the chamber and displaceable through the at least one aperture between the piston and the chamber to allow fluid to flow within the chamber between opposite sides of the piston. The variable viscosity fluid has a viscosity that is variable to vary an ability of the variable viscosity fluid to flow through the at least one aperture.

21 Claims, 16 Drawing Sheets

U.S. PATENT DOCUMENTS

| | | |
|---|---|---|
| 92,031 A | 6/1869 | Foster |
| 292,800 A | 2/1884 | Furrer |
| 497,026 A | 5/1893 | Judson |
| 1,001,641 A | 8/1911 | Harrison |
| 1,191,633 A | 5/1916 | Waggott |
| 1,289,580 A | 12/1918 | Vincenti |
| 1,779,765 A | 3/1930 | Eichhorn |
| 1,996,874 A | 8/1935 | Mascau |
| 2,036,830 A | 4/1936 | Rowley |
| 2,101,265 A | 12/1937 | Mercier |
| 2,379,538 A | 7/1945 | Meierhofer |
| 2,443,356 A | 4/1948 | Mathis |
| 2,453,969 A | 11/1948 | Carter |
| 2,470,480 A | 5/1949 | Fogg |
| 2,570,735 A | 10/1951 | Weise |
| 2,617,115 A | 11/1952 | Ellery |
| 2,640,200 A | 6/1953 | Wisbrun |
| 2,843,853 A | 7/1958 | Mauch |
| 2,973,969 A | 3/1961 | Thall |
| 3,206,235 A | 9/1965 | Albinson et al. |
| 3,379,430 A | 4/1968 | Ransom |
| 3,548,420 A | 12/1970 | Spence |
| 3,551,914 A | 1/1971 | Woodall |
| 3,754,286 A | 8/1973 | Ryan |
| 3,858,379 A | 1/1975 | Graves et al. |
| 3,871,032 A | 3/1975 | Karas |
| 3,874,004 A | 4/1975 | May |
| 3,906,552 A | 9/1975 | Weber |
| 3,920,610 A | 11/1975 | Wagner |
| 3,956,775 A | 5/1976 | Moore |
| 3,982,280 A | 9/1976 | Asbelle et al. |
| 4,089,072 A | 5/1978 | Glabiszewski |
| 4,328,594 A | 5/1982 | Campbell et al. |
| 4,442,554 A | 4/1984 | Copes |
| 4,506,395 A | 3/1985 | Haupt |
| 4,547,913 A | 10/1985 | Phillips |
| 4,606,332 A | 8/1986 | Gibson |
| 4,636,220 A | 1/1987 | Ziegelmeyer |
| 4,645,509 A | 2/1987 | Poggi et al. |
| 4,676,800 A | 6/1987 | Chen |
| 4,676,801 A | 6/1987 | Lundeen |
| 4,721,510 A | 1/1988 | Cooper et al. |
| 4,793,450 A | 12/1988 | Harrison |
| 4,822,363 A | 4/1989 | Phillips |
| 4,852,863 A | 8/1989 | Savenije |
| 4,865,611 A | 9/1989 | Al-Turaiki |
| 4,865,612 A | 9/1989 | Arbogast et al. |
| 4,869,476 A | 9/1989 | Shtarkman |
| 4,938,775 A | 7/1990 | Morgan |
| 4,959,073 A | 9/1990 | Merlette |
| 4,986,393 A | 1/1991 | Preukschat et al. |
| 5,019,109 A | 5/1991 | Voisin |
| 5,030,239 A | 7/1991 | Copes |
| 5,037,444 A | 8/1991 | Phillips |
| 5,062,859 A | 11/1991 | Naeder |
| 5,112,356 A | 5/1992 | Harris et al. |
| 5,116,383 A | 5/1992 | Shorter et al. |
| 5,116,384 A | 5/1992 | Wilson et al. |
| 5,156,632 A | 10/1992 | Wellershaus |
| 5,181,932 A | 1/1993 | Phillips |
| 5,181,933 A | 1/1993 | Phillips |
| 5,217,500 A | 6/1993 | Phillips |
| 5,219,365 A | 6/1993 | Sabolich |
| 5,258,039 A | 11/1993 | Goh et al. |
| 5,267,633 A | 12/1993 | Endo et al. |
| 5,290,319 A | 3/1994 | Phillips |
| 5,314,499 A | 5/1994 | Collier, Jr. |
| 5,376,133 A | 12/1994 | Gramnas |
| 5,376,139 A | 12/1994 | Pitkin |
| 5,376,141 A | 12/1994 | Phillips |
| 5,387,246 A | 2/1995 | Phillips |
| 5,425,781 A | 6/1995 | Allard et al. |
| 5,425,782 A | 6/1995 | Phillips |
| 5,443,528 A | 8/1995 | Allen |
| 5,443,529 A | 8/1995 | Phillips |
| 5,449,150 A | 9/1995 | Watanabe et al. |
| 5,458,656 A | 10/1995 | Phillips |
| 5,464,441 A | 11/1995 | Phillips |
| 5,482,513 A | 1/1996 | Wilson |
| 5,486,209 A | 1/1996 | Phillips |
| 5,507,838 A | 4/1996 | Chen |
| 5,509,936 A | 4/1996 | Rappoport et al. |
| 5,509,937 A | 4/1996 | Allard et al. |
| 5,509,938 A | 4/1996 | Phillips |
| 5,514,185 A | 5/1996 | Phillips |
| 5,514,186 A | 5/1996 | Phillips |
| 5,549,714 A | 8/1996 | Phillips |
| 5,571,210 A | 11/1996 | Lindh |
| 5,571,213 A | 11/1996 | Allen |
| 5,593,455 A | 1/1997 | Phillips |
| 5,593,456 A | 1/1997 | Merlette |
| 5,593,457 A | 1/1997 | Phillips |
| 5,645,138 A | 7/1997 | Tajima et al. |
| 5,653,767 A | 8/1997 | Allen et al. |
| 5,653,768 A | 8/1997 | Kania |
| 5,725,598 A | 3/1998 | Phillips |
| 5,728,175 A | 3/1998 | Rincoe |
| 5,728,176 A | 3/1998 | Phillips |
| 5,728,177 A | 3/1998 | Phillips |
| 5,746,774 A | 5/1998 | Kramer et al. |
| 5,766,265 A | 6/1998 | Phillips |
| 5,766,704 A | 6/1998 | Allen et al. |
| 5,769,896 A | 6/1998 | Rosendahl et al. |
| 5,776,205 A | 7/1998 | Phillips |
| 5,779,735 A | 7/1998 | Molino |
| 5,800,564 A | 9/1998 | Gelineau |
| 5,800,565 A | 9/1998 | Biedermann |
| 5,800,569 A | 9/1998 | Phillips |
| 5,824,112 A | 10/1998 | Phillips |
| 5,888,238 A | 3/1999 | Phillips et al. |
| 5,893,891 A | 4/1999 | Zahedi |
| 5,899,944 A | 5/1999 | Phillips |
| 5,913,902 A | 6/1999 | Geible |
| 5,944,760 A | 8/1999 | Christensen |
| 5,957,981 A | 9/1999 | Gramnas |
| 5,976,191 A | 11/1999 | Phillips |
| 5,993,488 A | 11/1999 | Phillips |
| 6,007,582 A | 12/1999 | May |
| 6,019,795 A | 2/2000 | Phillips |
| 6,071,313 A | 6/2000 | Phillips |
| 6,077,301 A | 6/2000 | Pusch |
| 6,099,572 A | 8/2000 | Mosler et al. |
| 6,120,547 A | 9/2000 | Christensen |
| 6,165,227 A | 12/2000 | Phillips |
| 6,187,052 B1 | 2/2001 | Molino et al. |
| 6,197,068 B1 | 3/2001 | Christensen |
| 6,206,934 B1 | 3/2001 | Phillips |
| 6,228,124 B1 | 5/2001 | Slemker et al. |
| 6,241,776 B1 | 6/2001 | Christensen |
| 6,254,643 B1 | 7/2001 | Phillips |
| 6,261,324 B1 | 7/2001 | Merlette |
| 6,280,479 B1 | 8/2001 | Phillips |
| 6,290,730 B1 | 9/2001 | Pitkin et al. |
| 6,306,178 B1 | 10/2001 | Kania et al. |
| 6,402,790 B1 | 6/2002 | Celebi |
| 6,406,500 B1 | 6/2002 | Phillips |
| 6,443,993 B1 | 9/2002 | Koniuk |
| 6,443,995 B1 | 9/2002 | Townsend et al. |
| 6,514,293 B1 | 2/2003 | Jang et al. |
| 6,562,075 B2 | 5/2003 | Townsend et al. |
| 6,596,029 B1 | 7/2003 | Gramnas |
| 6,602,295 B1 | 8/2003 | Doddroe et al. |
| 6,663,673 B2 | 12/2003 | Chirstensen |
| 6,669,737 B2 | 12/2003 | Mosler et al. |

| | | | |
|---|---|---|---|
| 6,676,708 B1 | 1/2004 | Laghi | |
| 6,740,125 B2 | 5/2004 | Mosler | |
| 6,793,683 B1 | 9/2004 | Laghi | |
| 6,805,717 B2 | 10/2004 | Christensen | |
| 6,869,451 B1 | 3/2005 | Laghi | |
| 6,875,241 B2 | 4/2005 | Christesen | |
| 6,875,242 B2 | 4/2005 | Christensen | |
| 6,887,279 B2 | 5/2005 | Phillips et al. | |
| 6,911,052 B2 | 6/2005 | Christensen | |
| 6,929,665 B2 | 8/2005 | Christensen | |
| 6,966,933 B2 | 11/2005 | Christensen | |
| 7,172,630 B2 | 2/2007 | Christensen | |
| 7,341,603 B2 | 3/2008 | Christensen | |
| 2002/0077706 A1 | 6/2002 | Phillips | |
| 2002/0133237 A1 | 9/2002 | Christensen | |
| 2003/0019540 A1 | 1/2003 | Townsend et al. | |
| 2003/0045944 A1 | 3/2003 | Mosler et al. | |
| 2004/0068326 A1 | 4/2004 | Christensen | |
| 2004/0162623 A1 | 8/2004 | Phillips | |
| 2005/0171618 A1 | 8/2005 | Christensen | |
| 2005/0203640 A1 | 9/2005 | Christensen | |
| 2006/0241783 A1 | 10/2006 | Christensen | |

FOREIGN PATENT DOCUMENTS

| | | |
|---|---|---|
| BR | 9304225 | 11/1995 |
| DE | 295807 | 12/1916 |
| EP | 0 948 947 | 10/1999 |
| EP | 1 149 568 | 10/2001 |
| EP | 1340478 | 9/2003 |
| GB | 1191633 | 5/1970 |
| GB | 1550658 | 11/1976 |
| GB | 2244006 | 11/1991 |
| IT | 556381 | 2/1957 |
| JP | 55112440 | 8/1980 |
| JP | 57040138 | 3/1982 |
| JP | 63231031 | 9/1988 |
| RU | 2033772 | 4/1995 |
| SU | 560606 | 6/1977 |
| WO | WO 94 10942 | 5/1994 |
| WO | WO 02 30340 | 4/2002 |
| WO | WO02/34173 | 5/2002 |
| WO | WO03/003953 | 1/2003 |

OTHER PUBLICATIONS www.oandp.org/jpo/library/2000_01_009.asp, "Comparison od the seattle lite foot and genesis II prosthetic foot during walking and running." Americann Academy of Orthotists and Prosthetists, 2000, pp. 9-14, vol. 12, No. 1.

Christensen, Roland J., U.S. Appl. No. 11/377,228, filed Mar. 15, 2006.

Christensen, Roland J., U.S. Appl. No. 11/377,229, filed Mar. 15, 2006.

Christensen, Roland J., U.S. Appl. No. 11/082,237, filed Mar. 15, 2006.

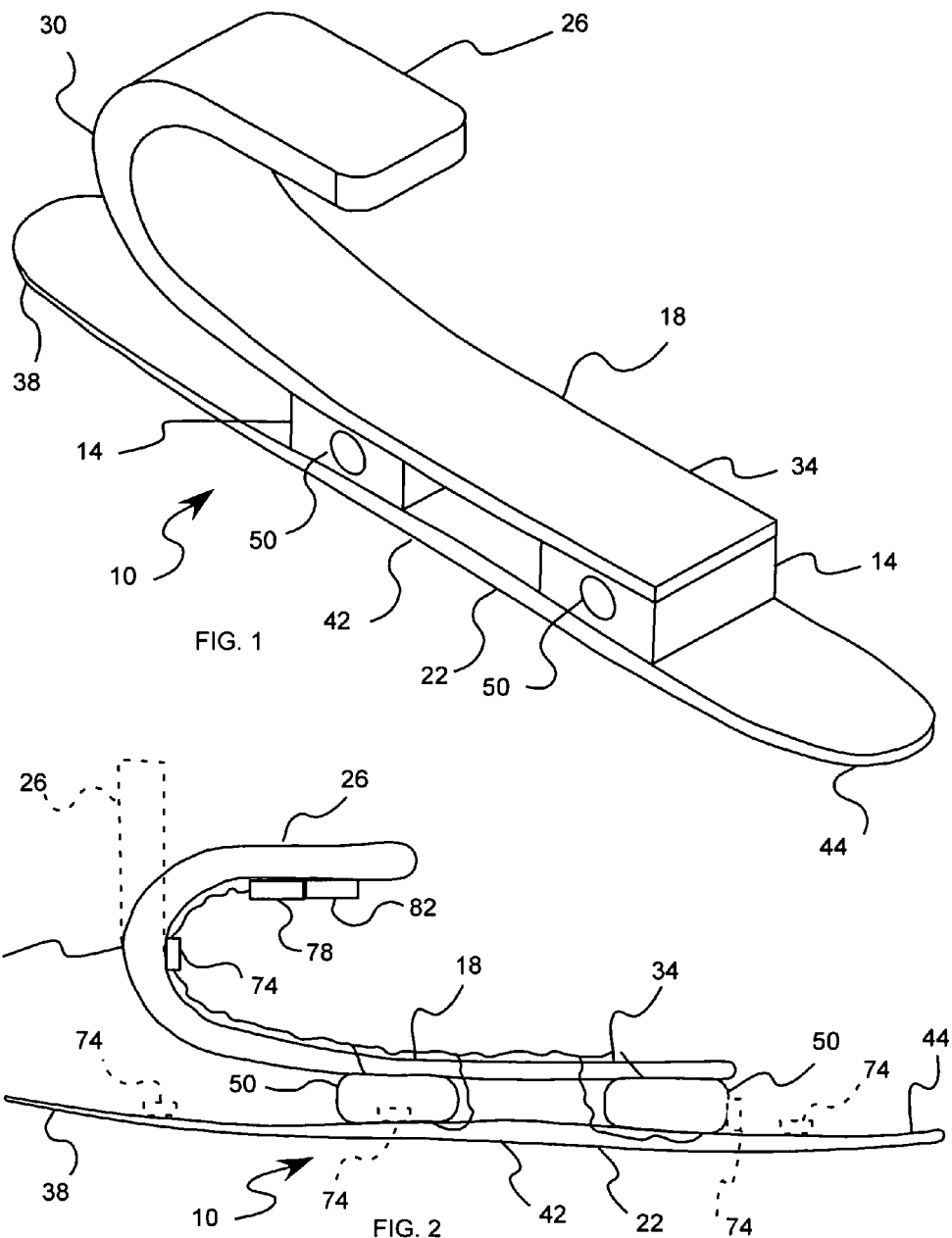

PROSTHETIC FOOT WITH ENERGY TRANSFER

This application is a continuation-in-part of U.S. patent application Ser. No. 11/377,228 filed Mar. 15, 2006 now U.S. Pat. No. 7,572,299 which is a continuation-in-part of U.S. patent application Ser. No. 11/098,828, filed Apr. 4, 2005, now U.S. Pat. No. 7,341,603 which is a continuation-in-part of U.S. application Ser. No. 10/738,645, U.S. Pat. No. 6,875,242, filed Dec. 16, 2003, which is a continuation of U.S. application Ser. No. 10/137,933, U.S. Pat. No. 6,663,673, filed May 3, 2002, which is a continuation-in-part of U.S. patent application Ser. No. 09/607,494, filed Jun. 30, 2000, now abandon, which are herein incorporated by reference.

BACKGROUND OF THE INVENTION

1. Field of the Invention

The present invention relates generally to prosthetic feet. More particularly, the present invention relates to prosthetic feet with an energy transfer mechanism.

2. Related Art

Many individuals have lost a limb for various reasons including war, accident, or disease. In most instances, these individuals are not only able to live relatively normal lives, but physically active lives as well. Often times, these individuals are aided in their everyday lives by a prosthetic limb. The objective of prosthesis is to provide an artificial limb that simulates the function and natural feel of the replaced limb.

With respect to prosthetic feet, the development of a functional and natural artificial foot has been limited only by material and imagination. Many designs have attempted to copy the anatomy of the foot or simulate its actions by replacing the bones and muscle with various mechanical components. Other designs have departed radically from mere anatomical copying or mechanical simulation by replacing the entire foot with an energy storage element, such as a spring. As the user steps onto the foot, the user's weight compresses the spring. As the user moves forward, the user's weight comes off the foot and the energy stored in the spring is used to propel the user forward. Examples of such energy storing, spring-like feet include U.S. Pat. Nos. 5,037,444; 4,547,913; 5,181,932 and 5,976,191.

The prosthetic feet typically include spring-like members that are typically flexible and resilient. In order to provide a natural feel and cushion of a natural foot, the members must be flexible and deflect under the user's weight. Such flexibility and the ability to deflect often require the members forming the foot to be structurally weak, or more flexible. On the other hand, it is desirable to make the members as strong or stiff as possible from a structural and durability standpoint. Thus, there may be a trade-off between obtaining a sufficient cushion or feel, with members that are weak or flexible and over-deflect, and obtaining a solid and durable structural foot, with stiffer members.

The stiffness of prosthetic feet typically varies according to the intended use. Feet intended for everyday use typically require a soft feel, and thus incorporate a softer spring. Feet intended for athletic use typically require strength, and thus incorporate a stiff spring. Feet designed for particular purposes are typically unsuited for other purposes. Stiff, athletic feet are too hard for everyday use, and soft, everyday feet are too fragile for athletic use. Multiple-use feet have been designed which are capable of many different uses, but without being particularly well suited for any specialized use.

In addition, users may have different weights. Thus, prosthetic feet may require a high degree of custom design, or be particularly tailored to the individual user. However, it is desirable from a cost and manufacturing standpoint to create a foot that is usable by many sizes of individuals.

SUMMARY OF THE INVENTION

It has been recognized that it would be advantageous to develop a prosthetic foot with adjustable stiffness for accommodating different uses or different users.

The invention provides a prosthetic foot device with variable stiffness response between first and second foot members. A chamber is associated with one of the first and second foot members, while a piston is associated with another of the first and second foot members and is movable in the chamber. At least one aperture is formed between the piston and the chamber. A variable viscosity fluid is disposed in the chamber and displaceable through the at least one aperture between the piston and the chamber to allow fluid to flow within the chamber between opposite sides of the piston. The variable viscosity fluid has a viscosity that is variable to vary an ability of the variable viscosity fluid to flow through the at least one aperture.

Additional features and advantages of the invention will be apparent from the detailed description which follows, taken in conjunction with the accompanying drawings, which together illustrate, by way of example, features of the invention.

BRIEF DESCRIPTION OF THE DRAWINGS

FIG. 1 is a perspective view of a prosthetic foot having an energy transfer medium with a variable viscosity fluid in accordance with an embodiment of the present invention;

FIG. 2 is a side view of another prosthetic foot having an energy transfer medium with variable viscosity fluid in accordance with another embodiment of the present invention;

DETAILED DESCRIPTION

Figure 2B:
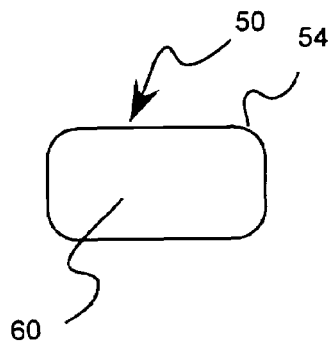
FIGS. 2b-2d are schematic views of an energy transfer medium including a shear stiffening material in accordance with an embodiment of the present invention.

Reference will now be made to the exemplary embodiments illustrated in the drawings, and specific language will be used herein to describe the same. It will nevertheless be understood that no limitation of the scope of the invention is thereby intended. Alterations and further modifications of the inventive features illustrated herein, and additional applications of the principles of the inventions as illustrated herein, which would occur to one skilled in the relevant art and having possession of this disclosure, are to be considered within the scope of the invention.

As illustrated in the figures, various embodiments of prosthetic feet in accordance with the present invention are shown with an energy transfer medium that includes a variable viscosity fluid or material, or an energy transfer mechanism. The energy transfer medium, or variable viscosity fluid or material, is located between first and second members of the foot so that energy is transferred between the first and second member, and thus through the energy transfer medium, during use. The variable viscosity of the fluid or material allows the energy transferred between the members to be varied, thus varying the stiffness or response of the foot. The variable viscosity fluid can increase in viscosity with an increase in a load factor applied to the variable viscosity fluid. Such load factors can include a load, a load rate, a strain, a strain rate, a pressure, a deflection, etc. As described in greater detail below, the variable viscosity fluid or material can include a shear stiffening material that increases in viscosity as load or strain, or load rate or strain rate, is applied; an electro rheologic fluid that changes viscosity under an applied electric field; or a magneto rheologic fluid that changes viscosity under an applied magnetic field. The energy transfer mechanism or variable resistance cell is disposed between primary and secondary foot members defining elongated springs.

As illustrated in FIG. 1, a prosthetic foot device, indicated generally at 10, in accordance with the present invention is shown with a variable energy transfer medium 14 for varying the stiffness or response of the foot device 10. As described above, the foot device 10 includes first and second members 18 and 22. The first member 18 is coupled to a stump of an amputee as is understood in the art, while the second member 22 is coupled to the first member 18, and positioned to operate between the first member and the ground. The first member 18 can be sized and shaped as a forefoot or upper foot member that extends from an attachment portion 26, which is coupled to a stump of an amputee, downwardly and forwardly through an arcuate portion 30, to a coupling section 34 coupled to the second member 22. The second member 22 can be sized and shaped as a full-length sole or lower foot member that extends from a heel portion 38, through a coupling section 42 coupled to the first member 18, to a toe portion 44. It is believed that the configuration of the second member 22 as a full-length lower foot member provides a smoother gait.

The attachment portion 26 of the first member 18 can attach to a socket for receiving the stump of the amputee, as is known in the art. The socket is configured for the specific needs of the amputee, but typically has a portion adapted for standard attachment. The attachment portion 26 can be attached to the socket by any means, such as by nut and bolt, again as is known in the art. The first member 18 can be curved in a general C-shape, with the socket attaching to a top of the attachment portion 26 forming a horizontal attachment. Alternatively, a first member can be curved in a general L-shape or a J-shape, with the socket attaching to the side of the attachment portion forming a vertical attachment, as shown in dashed lines in FIG. 2.

The heel portion 38 of the second member 22 can be located at a heel location in a region near the rear of the foot device 10 where the heel of a natural foot would be located. Similarly, the toe portion 44 is located at a toe location in a region near the front of the foot device 10 where the toes of a natural foot would be located.

The first and second members 18 and 22 can be resilient and energy storing foot members that deflect or flex, storing energy, much like a leaf spring. Thus, the first and second members 18 and 22 can be formed of a flexible and resilient material that allows the foot members to deflect or flex. In one aspect, the members 18 and 22 can be formed of a fiber reinforced resin material, such as a graphite-reinforced resin.

The first member 18 can be disposed above, and spaced-apart from, the second member 22, such that the members 18 and 22 are in a non-contacting relationship, or are not directly attached. The energy transfer medium 14 can be disposed between, and can separate, the members 18 and 22. The energy transfer medium 14 can be more flexible than the energy-storing members 18 and 22, and allows the members 18 and 22 to move with respect to one another. In addition, the energy transfer medium 14 allows the members 18 and 22 to deflect or flex, and allows a greater range of motion of the members. The energy transfer medium 14 can include a resilient and compliant material, such as rubber or urethane. Thus, the energy transfer medium 14 can provide a cushioned, softer, and less stiff feel to the foot device 10, making the foot device more comfortable and natural. The addition of the energy transfer medium 14 also advantageously allows the first and second members 18 and 22 to be stiffer and stronger, while still providing a softer, cushioned feel. Thus, the stiffer stronger members 18 and 22 can be more durable. Various aspects of a prosthetic foot with an energy transfer medium are disclosed in U.S. patent application Ser. No. 09/607,494, which is herein incorporated by reference.

The energy transfer medium 14 also advantageously includes a variable viscosity fluid or material 50. The variable viscosity fluid 50 can be included in pockets or cavities formed in the energy transfer medium, as shown in FIG. 1, or can form substantially the entire energy transfer medium, as shown in FIG. 2. The energy transfer medium 14 and/or the variable viscosity fluid 50 transfer energy from the second member 22 to the first member 18 during use, as described in greater detail below. The variable viscosity fluid or material 50 can be disposed or contained in flexible bags or bladders 54.

Figure 2C:
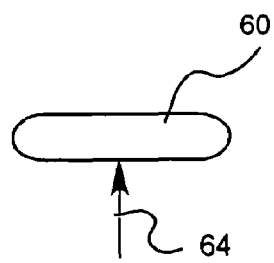
Figure 2D:
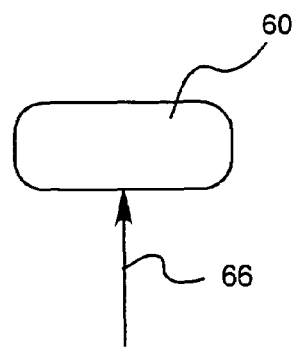

Referring to FIGS. 2b-2d, the variable viscosity fluid or material 50 can include a shear stiffening material 60. Such a shear stiffening material 60 increases in viscosity as a load or strain (or load or strain rate) is applied, or as the load or strain increases. An example of such shear stiffening material is a composition of cornstarch and water. Under little or no load or strain (indicated by arrow 64), the shear stiffening material 60 can be less viscous and capable of greater flow, and thus can be displaceable while the energy transfer medium can be compressible, as shown in FIG. 2c. Under greater load or strain (indicated by arrow 66), the shear stiffening material 60 can be more viscous and less capable of flowing, and thus can be less displaceable while the energy transfer medium can be less compressible, as shown in FIG. 2d. It will be appreciated that the less-viscous shear stiffening material dissipates more energy or force so that less energy or force is transferred by the material. Similarly, the more-viscous shear stiffening material transfers more energy or force.

Figure 2E:
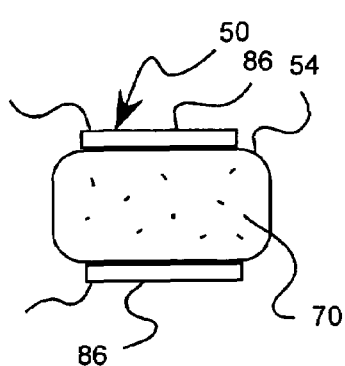
FIGS. 2e-2g are schematic views of an energy transfer medium including an electro rheologic material in accordance with an embodiment of the present invention.
Figure 2F:
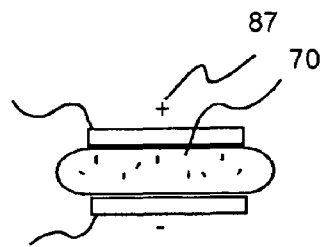
Figure 2G:
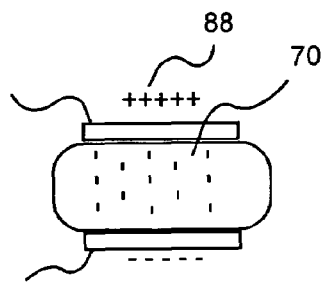

Referring to FIGS. 2e-2g, the variable viscosity fluid or material 50 can include an electro rheologic fluid 70 that is responsive to an applied electric field to alter its viscosity. Such an electro rheologic fluid 70 increases in viscosity as an electric field is applied. Under little or no electric field (indicated at 87), the electro rheologic fluid 70 can be less viscous and capable of greater flow, and thus can be displaceable, as shown in FIG. 2f. Under a greater electric field (indicated at 88), the electro rheologic fluid 70 can be more viscous and less capable of flowing, and thus can be less displaceable, as shown in FIG. 2g. Again, it will be appreciated that the less-viscous electro rheologic fluid dissipates more energy or force so that less energy or force is transferred by the fluid. Similarly, the more-viscous electro rheologic fluid transfers more energy or force.

Referring again to FIG. 2, the foot device 10 can include a transducer 74, such as a strain gauge, coupled to the first and/or second member 18 and/or 22. The transducer 74 senses strain or deformation in the member 18 and/or 22. The transducer 74 can be operatively coupled to control electronics 78 and a power source 82. The control electronics 78 and transducer 74 can be operatively coupled to the electro rheologic fluid, such as by electrodes 86 (FIG. 2e) coupled to the bag 54. The control electronics 78 can include amplifier circuitry, while the power source 82 can be a battery. The transducer 74 senses deflection or strain in the first and/or second members 18 and 22 and produces a signal that can be sent to the control electronics 78. The control electronics 78 can include amplifier circuitry to amplify the signal to create a control signal. In addition, the control electronics 78 can include circuitry to accept only signals that correspond to a predetermined minimum strain or deflection. The control signal can be applied to the electro rheologic fluid 70 by the electrodes 86 (FIG. 2e). It will be appreciated that the control electronics 78 can include inputs to vary the amplification, minimums, etc., to control or customize the energy transfer of the fluid, and the stiffness of the foot device.

Alternatively, the transducer 74 can be coupled to the energy transfer medium 14, or the bag or bladder 54 containing the variable viscosity fluid 50. Thus, the transducer 74 can be configured to sense pressure of the variable viscosity fluid 50 in the bladder 54. Similarly, the transducer 74 can be configured to sense deflection of the energy transfer medium 14.

Referring to FIGS. 2e-2g, such an electro rheologic fluid 70 can include particles or filings in an oil. As the electric field 88 is applied, the particles or filings align, increasing the viscosity of the fluid 70, or the oil with particles or filings. With no or little electrical field 87, the particles or filings are random, decreasing the viscosity of the fluid 70, or the oil with particles or filings.

Figure 2H:
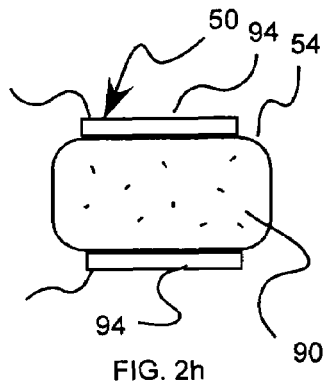
FIGS. 2h-2j are schematic views of an energy transfer medium including a magneto rheologic material in accordance with an embodiment of the present invention.
Figure 2I:
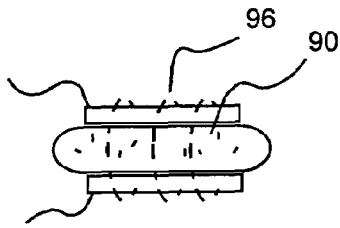
Figure 2J:
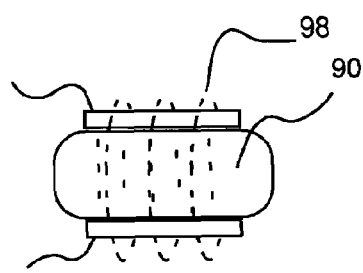

Referring to FIGS. 2h-2j, the variable viscosity fluid or material 50 can include a magneto rheologic fluid 90 that is responsive to an applied magnetic field to alter its viscosity. Such a magneto rheologic fluid 90 increases in viscosity as a magnetic field is applied. Under little or no magnetic field (represented by lines 96), the magneto rheologic fluid 90 can be less viscous and capable of greater flow, and thus can be displaceable, as shown in FIG. 2i. Under a greater magnetic field (represented by lines 98), the magneto rheologic fluid 90 can be more viscous and less capable of flowing, and thus can be less displaceable, as shown in FIG. 2j. Again, it will be appreciated that the less-viscous magneto rheologic fluid dissipates more energy or force so that less energy or force is transferred by the fluid. Similarly, the more-viscous magneto rheologic fluid transfers more energy or force.

The magnetic field can be applied by magnets 94 that are operatively coupled to the bag 54. The magnets 94 can be electro-magnets operatively coupled to the control electronics 78 (FIG. 2) using the control signal to generate the magnetic field. Such a magneto rheologic fluid 90 can include particles or filings in an oil. As the magnetic field 98 is applied, the particles or filings align, increasing the viscosity of the fluid, or the oil with particles or filings. With little or no magnetic field 96, the particles or filings are random, decreasing the viscosity of the fluid, or the oil with particles or filings.

Figure 2K:
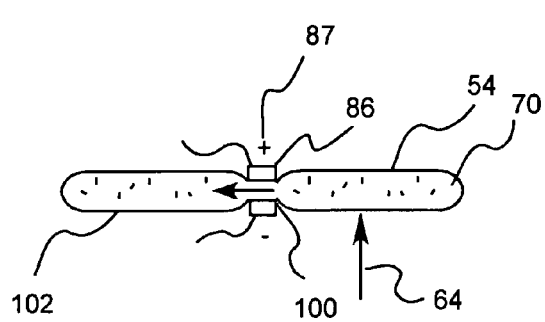
FIGS. 2k and 2l are schematic views of an energy transfer medium including an electro rheologic material in accordance with an embodiment of the present invention.
Figure 2L:
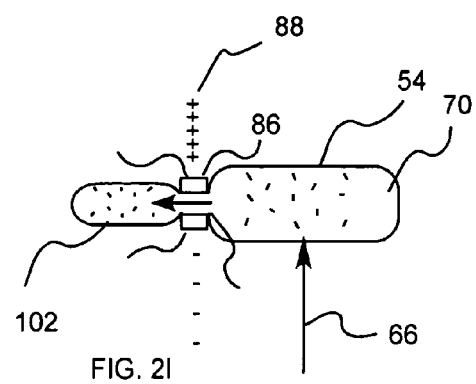

Referring to FIGS. 2k and 2l, the electro rheologic fluid 70 can be forced through, or can pass through, an orifice 100 and into a reservoir 102 under the loading of the foot. The electrodes 86 can be disposed around the orifice 100 to apply and electric field at or near the orifice. The electro rheologic fluid 70 is responsive to the applied electric field to alter its viscosity. Such an electro rheologic fluid 70 increases in viscosity as the electric field is applied, thus impeding the flow of the fluid 70 through the orifice. Under little or no electric field (indicated at 87), the electro rheologic fluid 70 can be less viscous and capable of greater flow, and thus can pass through the orifice 100, as shown in FIG. 2k. Therefore, under lesser force or load 64, the fluid 70 flows through the orifice 100 for less energy transfer, and a softer feel. Under a greater electric field (indicated at 88), the electro rheologic fluid 70 can be more viscous and less capable of flowing, and thus is impeded from flowing through the orifice 100, as shown in FIG. 2l. Therefore, under greater force or load 66, the fluid 70 is impeded from flowing through the orifice 100 for more energy transfer and a stiffer feel.

Figure 2M:
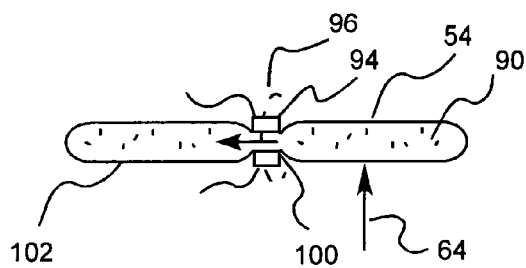
FIGS. 2m and 2n are schematic views of an energy transfer medium including a magneto rheologic material in accordance with an embodiment of the present invention.
Figure 2N:
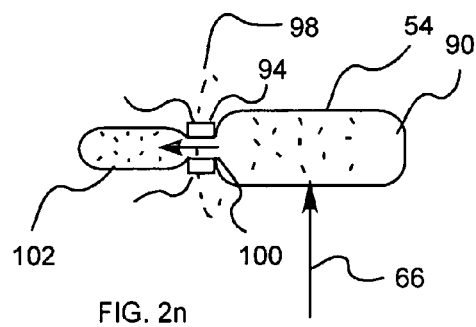

Referring to FIGS. 2m and 2n, the magneto rheologic fluid 90 can be forced through, or can pass through, an orifice 100 and into a reservoir 102 under the loading of the foot. The magnets 94 can be disposed around the orifice 100 to apply a magnetic field at or near the orifice. The magneto rheologic fluid 90 is responsive to the applied magnetic field to alter its viscosity. Such a magneto rheologic fluid 90 increases in viscosity as the magnetic field is applied, thus impeding the flow of the fluid 90 through the orifice. Under little or no magnetic field (indicated at 96), the magneto rheologic fluid 90 can be less viscous and capable of greater flow, and thus can pass through the orifice 100, as shown in FIG. 2m. Therefore, under lesser force or load 64, the fluid 90 flows through the orifice 100 for less energy transfer, and a softer feel. Under a greater magnetic field (indicated at 98), the magneto rheologic fluid 90 can be more viscous and less capable of flowing, and thus is impeded from flowing through the orifice 100, as shown in FIG. 2n. Therefore, under greater force or load 66, the fluid 90 is impeded from flowing through the orifice 100 for more energy transfer and a stiffer feel.

Figure 3A:
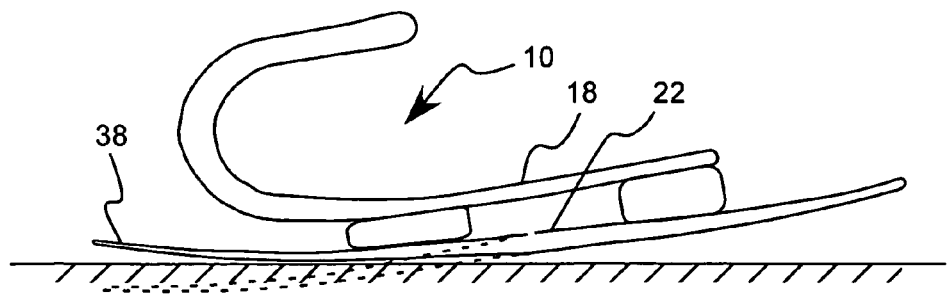
FIGS. 3a-3d are side schematic views of the prosthetic foot of FIG. 2 demonstrating the operation of prosthetic foot.
Figure 3B:
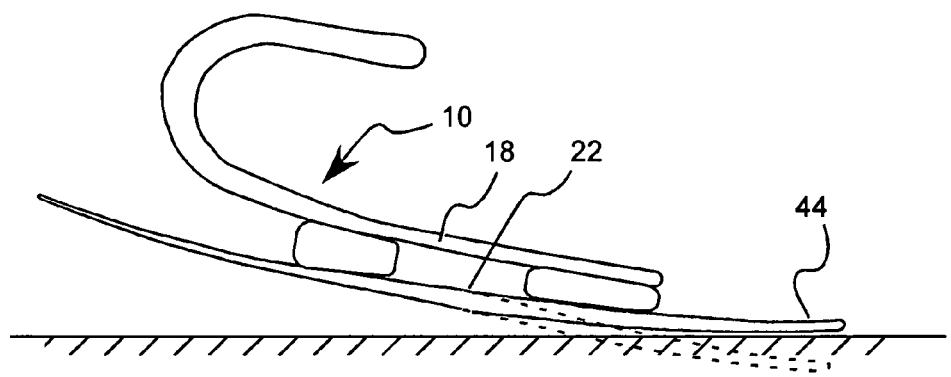
Figure 3C:
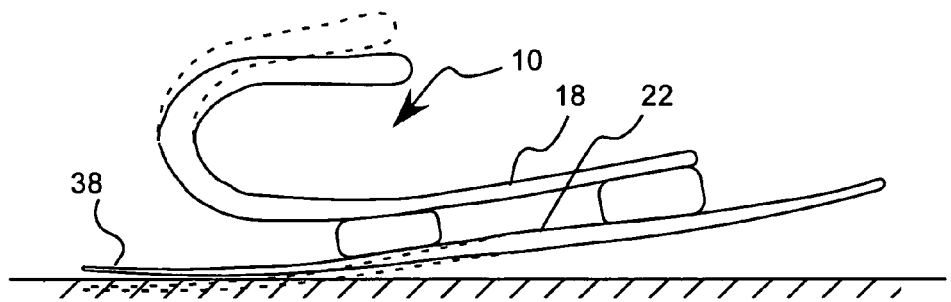
Figure 3D:
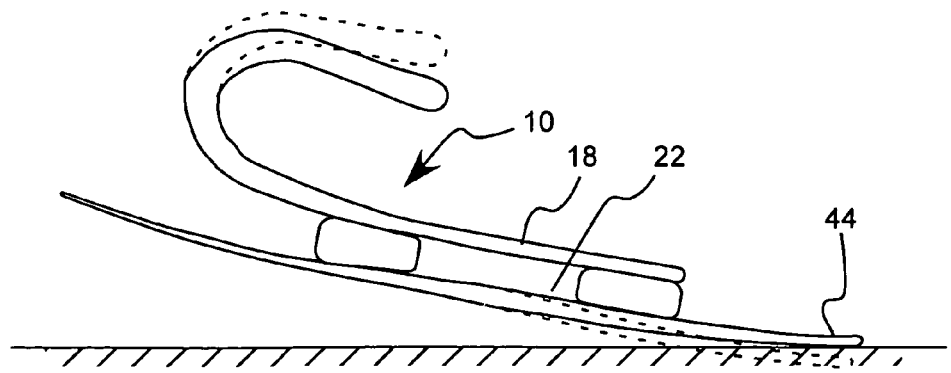

Referring to FIGS. 3a-3d, the operation of the foot device 10 is illustrated, with a lower force application, such as walking, illustrated in FIGS. 3a and 3b, and with a higher force application, such as running, illustrated in FIGS. 3c and 3d. Referring to FIG. 3a, as the user steps on the foot device 10, an applied force, such as the user's weight, causes the heel portion 38 of the second member 22 to deflect (indicated by the solid and dashed lines). The secondary member 22 applies a force to the energy transfer medium 14 and variable viscosity fluid that may be a lesser force due to the operation of the foot device 10 in a walking application. The energy transfer medium 14 compresses to a greater extent, dissipating some of the force, and transferring less force to the first member 18. Thus, the energy transfer medium 14 or variable viscosity fluid allows the second member 22 or heel portion 38 to deflect and/or move with respect to the first member 18, providing a soft, cushioned feel.

Referring to FIG. 3b, as the user continues to step, or walk, on the foot device 10, the toe portion 44 of the second member 22 deflects (indicated by the solid and dashed lines). Again, the secondary member 22 applies a force to the energy transfer medium 14 and variable viscosity fluid that may be a lesser force due to the operation of the foot device 10 in a walking application. The energy transfer medium 14 compresses to a greater extend, dissipating some of the force, and transferring less force to the first member 18. Again, the energy transfer medium 14 or variable viscosity fluid allows the second member 22 or toe portion 44 to deflect and/or move with respect to the first member 18, providing a soft, cushioned feel.

Referring to FIG. 3c, as the user exerts a greater force on the foot device 10, such as by running, the heel portion 38 of the second member 22 deflects (indicated by the solid and dashed lines). The secondary member 22 applies a force to the energy transfer medium 14 and variable viscosity fluid that may be a greater force due to the operation of the foot device 10 in a running application. The energy transfer medium 14 and variable viscosity fluid dissipate less or no force, and transfers more or all of the force to the first member 18. As described above, the variable viscosity fluid can be a shear stiffening material that increases viscosity due to the applied load or strain. Or the variable viscosity fluid can be a magneto or electro rheologic fluid that increases viscosity due to the application of a magnetic or electric field corresponding to the strain or deflection sensed by the transducer. Thus, the energy transfer medium 14 or variable viscosity fluid transfers the energy or force from the second member 22 to the first member 18 causing the first member 18 to deflect, indicated by the dashed and solid lines. Therefore, in a higher load application, or running, both the first and second members 18 and 22 can be more fully utilized.

Referring to FIG. 3d, as the user continues to run on the foot device 10, the toe portion 44 of the second member 22 deflects (indicated by the solid and dashed lines). The secondary member 22 applies a force to the energy transfer medium 14 and variable viscosity fluid that may be a greater force due to the operation of the foot device 10 in a running application. The energy transfer medium 14 and variable viscosity fluid transfer more force to the first member 18 causing the first member 18 to deflect (indicated by the dashed and solid lines). Again, in a higher load application, both the first and second members 18 and 22 can be more fully utilized.

Because the first and second members 18 and 22 can be made of a resilient material, the members 18 and 22 act as springs and store the energy to be subsequently released. As the user lifts the foot 10, the toe portion 44 of the foot 10 returns to its original position, pushing-off.

Figure 4:
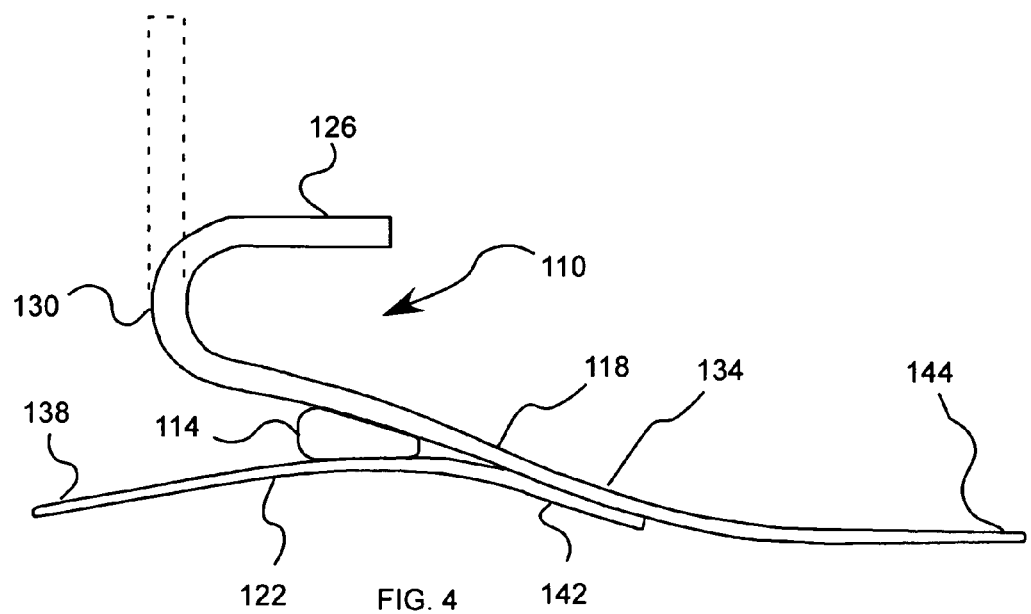
FIG. 4 is a side view of another prosthetic foot having an energy transfer medium with variable viscosity fluid in accordance with another embodiment of the present invention.

Referring to FIG. 4, another prosthetic foot device 110 is shown with an energy transfer medium 114. The energy transfer medium 114 can be similar to that described above, including a variable viscosity fluid or material. The foot device 110, however, has first and second members 118 and 122 with a different configuration than that described above. The first member 118 can be an upper or forefoot member with an attachment section 126 (horizontal shown in solid lines, vertical shown in dashed lines), curving downwardly and forwardly through a curvilinear spring or ankle section 130, an arch section 134, and a toe section 144 at a toe location of toes of a natural foot. Thus, the first member 118 can have a general C-shape or a J-shape. The second member 122 can be a lower heel member and can have an attachment section 142 attached to the arch section 134 of the first member 118, and extending rearwardly towards a heel section 138 at a heel location of a natural heel. The first and second members 118 and 122 can be resilient and energy storing foot members that deflect or flex, storing energy, and can be formed of a fiber reinforced resin material, such as a graphite-reinforced resin. The energy transfer medium 114 can be disposed between the first and second members 118 and 122, and can operate as described above.

Figure 5:
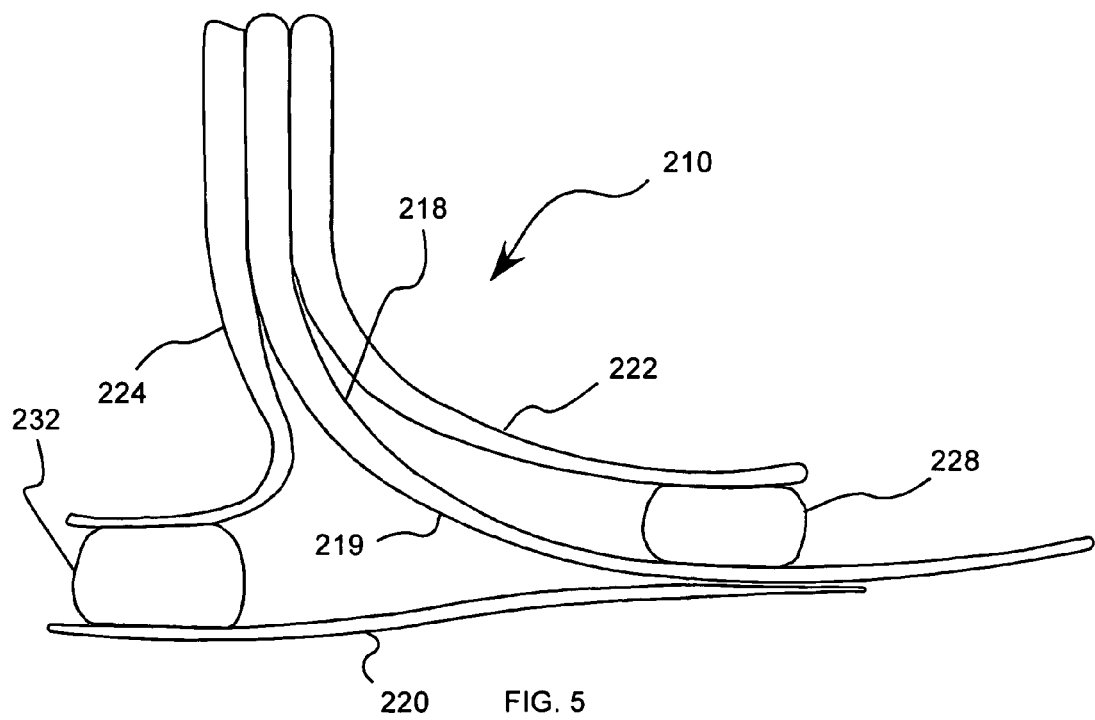
FIG. 5 is a side view of another prosthetic foot having an energy transfer medium with variable viscosity fluid in accordance with another embodiment of the present invention.

Referring to FIG. 5, another prosthetic foot device 210 is shown which is similar in many respects to the foot device 110 shown in FIG. 4 and described above. The foot device 210 can include a first member 218 that can include both 1) an upper forefoot member 219, and 2) a lower heel member 220, as described above. In addition, the foot device 210 can include a second member that can be a forefoot and/or heel reinforcement member 222 and/or 224. The forefoot reinforcement member 224 can have an attachment section attached to the first member 218 or socket, and extend downwardly and forwardly in a curvilinear fashion above the upper forefoot member 219 of the first member 218. A forefoot energy transfer medium 228 can be disposed between the first and second members 218 and 222, or between the upper forefoot member 219 and the forefoot reinforcement member 222. Similarly, the lower heel reinforcement member 224 can include an attachment section attached to the first member 218 or socket, and extend downwardly and rearwardly in a curvilinear fashion above the lower heel member 220 of the first member 218. A heel energy transfer medium 232 can be disposed between the first and second members 218 and 224, or between the lower heel member 220 and the heel reinforcement member 224. The various members 219, 220, 222 and 224 can be resilient and energy storing foot members that deflect or flex, storing energy, and can be formed of a fiber reinforced resin material, such as a graphite-reinforced resin.

Figure 6A:
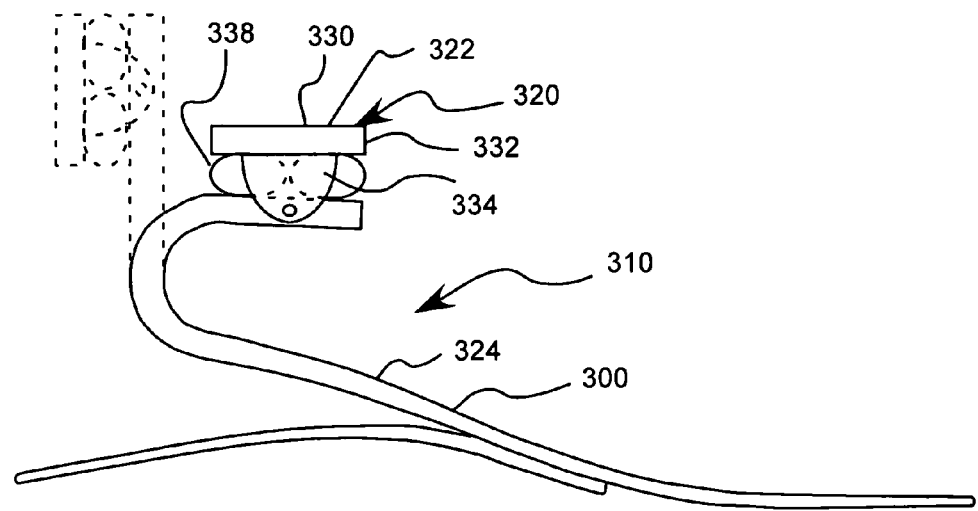
FIG. 6a is a side view of another prosthetic foot having an energy transfer medium with variable viscosity fluid in accordance with another embodiment of the present invention.
Figure 6B:
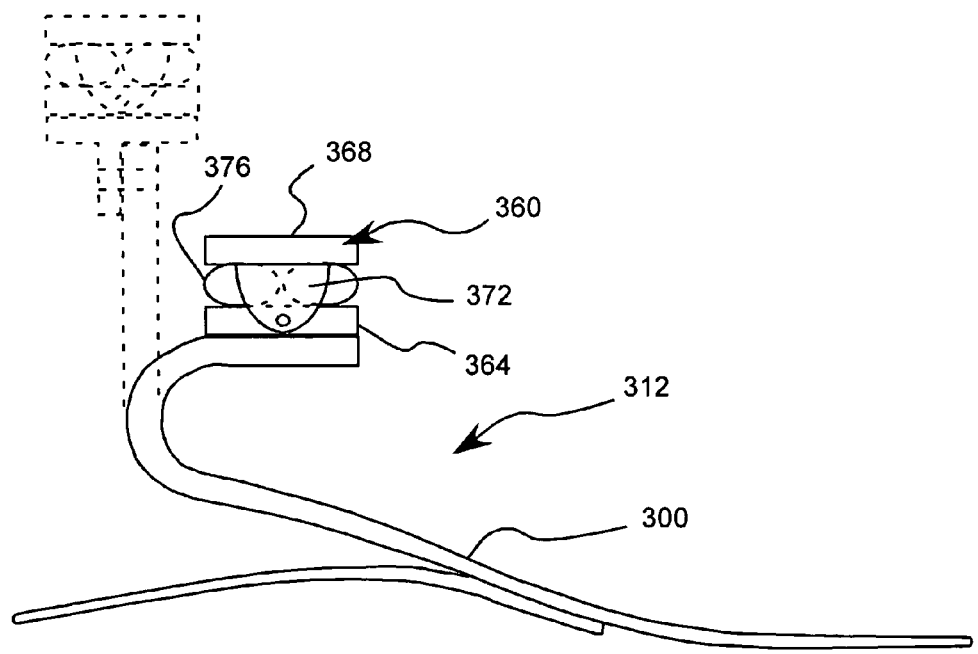
FIG. 6b is a side view of another prosthetic foot having an energy transfer medium with variable viscosity fluid in accordance with another embodiment of the present invention.

Referring to FIGS. 6a and 6b, a prosthetic foot 300 is shown with adaptors to convert the prosthetic foot 300 into a prosthetic foot device 310 and 312 with a variable energy transfer medium. The prosthetic foot 300 shown in FIGS. 6 and 7 is similar to the prosthetic foot device shown in FIG. 4 and described above. It will be appreciated, however, that the adaptors can be used with various different configurations, such as those shown in FIGS. 2 and 5.

Referring to FIG. 6a, an adaptor 320 is coupled to the prosthetic foot 300 such that the adaptor 320 forms a first member 322, and the prosthetic foot 300 forms the second member 324. The foot 300 can be resilient and energy storing foot member that deflects or flexes, storing energy, and can be formed of a fiber reinforced resin material, such as a graphite-reinforced resin. The adaptor 320 can attach in a horizontal manner to a horizontal attachment section of the prosthetic foot, as shown in solid lines, or in a vertical manner to a vertical attachment section of the prosthetic foot, as show in dashed lines. (It will of course be appreciated that the adaptor can be attached at any angle, and the horizontal and vertical are shown as typical attachments.)

The adaptor 320 can include a bracket 330 pivotally coupled to the foot 300 or attachment section. The bracket 330 can include a base 332 and a pair of arms 334 extending therefrom with distal ends pivotally coupled to the foot 300. An energy transfer medium 338 similar to those described above with a variable viscosity fluid or material can be disposed between the first member 322 or adaptor 320 and the second member 324 or foot 300. Therefore, the adaptor 320 advantageously adds the energy transfer medium 338 to the prosthetic foot 300.

Referring to FIG. 6b, an adaptor 360 is shown that is similar to the adaptor shown in FIG. 6a, and described above. The adaptor 360 further includes an attachment plate 364 for attachment to the foot 300. The foot 300 can be resilient and energy storing foot member that deflects or flexes, storing energy, and can be formed of a fiber reinforced resin material, such as a graphite-reinforced resin. The adaptor 360 can include a similar base 368 with arms 372 extending therefrom and pivotally attached to the attachment plate 364. An energy transfer medium 376 is disposed between the base 368 and the attachment plate 364. Thus, the adaptor 360 can be coupled to the foot without having a pivotal attachment directly on the foot itself.

Figures 6C, 6D:
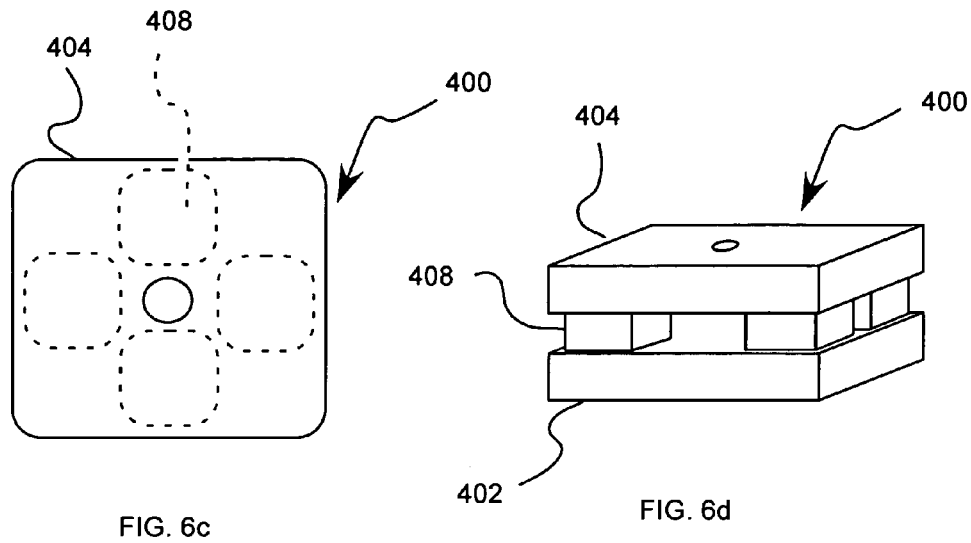
FIG. 6c is a partial top view of another prosthetic foot having an energy transfer medium with variable viscosity fluid in accordance with another embodiment of the present invention.
FIG. 6d is a partial perspective view of another prosthetic foot having an energy transfer medium with variable viscosity fluid in accordance with another embodiment of the present invention.
Figure 7:
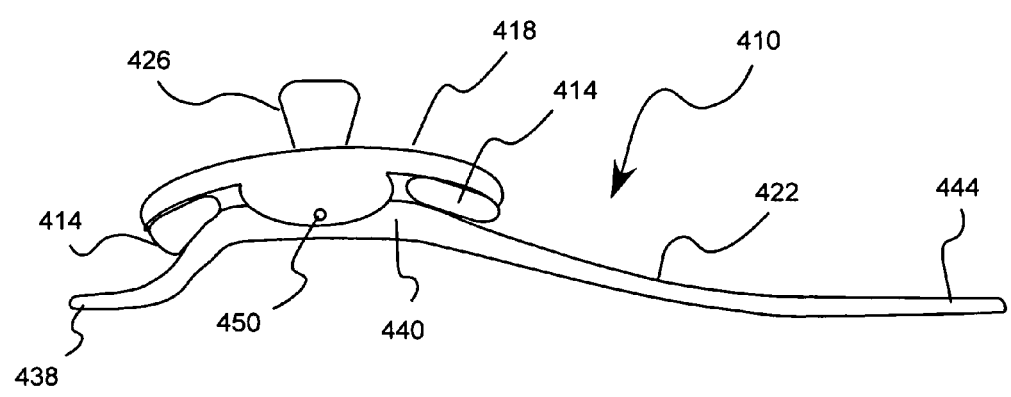
FIG. 7 is a side view of another prosthetic foot having an energy transfer medium with variable viscosity fluid in accordance with another embodiment of the present invention.

Referring to FIGS. 6c and 6d, an adaptor 400 is shown that is similar in many respects to the adaptors described above. The adaptor 400 advantageously can allow the foot or members to pivot in both 1) a longitudinal (or forward and rearward) direction, and 2) a lateral direction. The adaptor 400 can include an attachment plate 402 for attachment to the foot, similar to that described above. The adaptor can include a base 404 that is coupled to the attachment plate 402, such is by a pin, so that the base 404 and the attachment member 402 can pivot with respect to one another. An energy transfer medium 408, similar to those described above, can be disposed between the base 404 and the attachment plate 402. The energy transfer medium 408 can be disposed in various configurations, including in longitudinal and lateral alignment, as shown FIG. 6c, or in opposite corners, as shown in FIG. 6d.

Referring to FIG. 7, another prosthetic foot device 410 is shown with an energy transfer medium 414. The energy transfer medium 414 can be similar to that described above, including a variable viscosity fluid or material. The foot device 410 also includes first and second members 418 and 422 with a different configuration than that described above. The first member 418 can be an upper attachment member with an attachment section 426 for coupling to a stump of an amputee. The second member 422 can include a lower foot member with an attachment section 440 curving both 1) downwardly and forwardly to a toe section 444 at a toe location of toes of a natural foot, and 2) downwardly and rearwardly to a heel section 438 at a heel location of a natural heel. The second member 422 can be pivotally attached to the first member 418, such as with a pivot pin 450. The second member 422 can be resilient and energy storing foot member that deflects or flexes, storing energy, and can be formed of a fiber reinforced resin material, such as a graphite-reinforced resin. The energy transfer medium 414 can be disposed between the first and second members 418 and 422, and can operate as described above.

In use, the second member 440 can pivot about the pivot pin 450 with respect to the first member 418. The energy transfer medium 414 can include a variable viscosity fluid as described above to adjust the feel or softness of the foot.

Referring to FIGS. 8a-11, prosthetic foot devices are shown with an energy transfer mechanism or variable resistance cell that variably resists flow of a fluid through a variable orifice. The energy transfer mechanism or variable resistance cell can be disposed between primary and secondary foot members that define primary and secondary elongated springs. Thus, the primary foot member can be a forefoot member extending to a toe location of a natural toe and/or a heel member extending to a heel location of a natural heel, while the secondary foot member can be a forefoot reinforcement member and/or a heel reinforcement member. As an applied load is applied to the primary foot member (such as the heel member and/or forefoot member) the primary foot member defines a spring that deflects and stores energy, and provides a resistance response to the applied force. The primary and secondary foot members, including the forefoot member, the forefoot reinforcement member, the heel member and the heel reinforcement member can be formed of a composite material, such as a carbon fiber in a resin matrix.

The energy transfer mechanism or variable resistance cell variably transfers energy to the secondary foot member (such as the heel and/or forefoot reinforcement members). The secondary foot member also defines a spring, and thus deflects and stores energy, and provides an additional resistance response. Therefore, the overall resistance response applied by the foot (and stiffness or feel of the foot) is a combination of the primary and secondary foot members, and varies based on the amount of energy or applied load transferred from the primary foot member to the secondary foot member by the energy transfer mechanism or variable resistance cell. The energy transfer mechanism or variable resistance cell is configured to transfer a greater amount of energy or load from the primary to the secondary foot member in response to a greater applied load, thus providing a stiffer feel and greater resistance response. Thus, the variable orifice can reduce in size to increase resistance to the flow of fluid. Conversely, the energy transfer mechanism or variable resistance cell is configured to transfer a lesser amount or energy or load from the primary to the secondary foot member in response to a lesser applied load, thus providing a softer feel and a lesser resistance response. Thus, the variable orifice can increase in size to decrease resistance to the flow of fluid. Various aspects of a variable resistance cell are described in U.S. Pat. No. 6,875,241, filed Feb. 5, 2003, and U.S. patent application Ser. No. 11/082,237, filed Mar. 16, 2005, which are herein incorporated by reference.

Figure 8A:
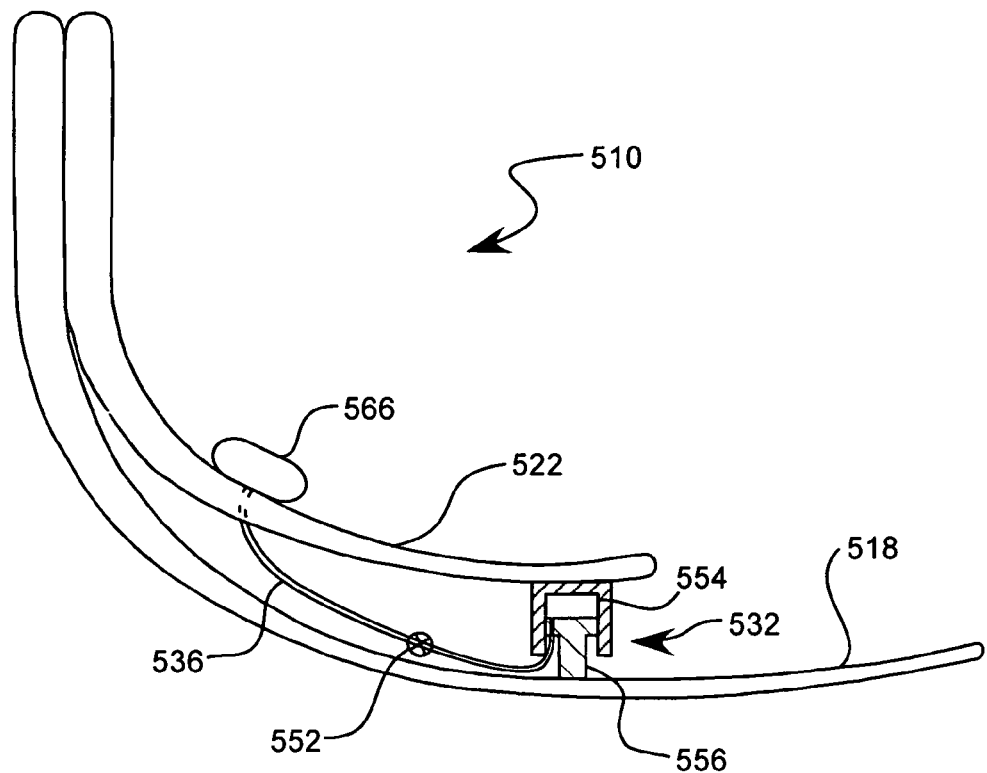
FIG. 8a is a side view of another prosthetic foot having an energy transfer mechanism or a variable resistance cell in accordance with another embodiment of the present invention.

Referring to FIGS. 8a and b, another prosthetic foot device 510 (FIG. 8a) or 512 (FIG. 8b) is shown which is similar in many respects to those described above. The foot device 510 can include a primary elongated foot or forefoot member 518 and a secondary foot or reinforcement member 522. The primary elongated foot member 518 can be attached to the stump of an amputee, and can extend therefrom to a toe location of a natural toe, and can form an elongated resilient spring that can store energy during deflection and resist forces applied to the primary foot member 518. The secondary foot member 522 can also be an elongated resilient spring that can store energy during deflection and can be adjacent to and receive applied loads from the primary foot member 518. For example, the secondary foot or reinforcement member 522 can be attached to the stump of an amputee and/or coupled to the primary foot member, and can extend above the primary foot member, as shown.

The foot device can include means for variably transferring energy between the primary foot member 518 and the secondary foot member 522 during use. The means for variably transferring energy can increase resistance against the forces applied to the primary foot member 518 when the forces increase so that more load can be transferred between the primary foot member 518 and the secondary foot member 522. The means for variably transferring energy can also decrease resistance against the forces applied to the primary foot member 518 when the forces decrease so that less load is transferred between the primary foot member 518 and the secondary foot member 522.

The means for variably transferring energy can be disposed between the primary elongated foot member 518 and the secondary foot member 522, and can include an enclosure 532 disposed between the primary foot member 518 and the secondary foot member 522, and a fluid path 536 that is in fluid communication with the enclosure 532. The fluid path 536 can also be in fluid communication with a reservoir 566. A fluid can be disposed in the enclosure 532 and reservoir 566 so that fluid can flow between the enclosure 532, and the reservoir 566, through the fluid path 536. The fluid can be a substantially incompressible fluid, such as oil. Alternatively, the fluid can be a variable viscosity fluid as discussed above.

The means for variably transferring energy can also include means for variably resisting fluid flow between the enclosure 532 and the reservoir 566 so that the force applied to the primary foot member 518 can be variably transferred to the secondary foot member 522. The means for variably resisting fluid flow can include a variable orifice 552 operatively disposed in the fluid path 536 and can provide variable resistance against fluid flow through the fluid path 536. The variable orifice 552 can be any variably sizable flow restriction device such as a servo-valve, a check valve, a needle valve, or a gate valve, as is generally known in the art.

The variable orifice 552 can variably resist the flow of fluid out of the enclosure 532 so that the enclosure can variably transfer energy between the primary elongated foot member 518 and the secondary foot member 522 during use. The variable orifice 552 can increase resistance to fluid flow between the enclosure 532 and the reservoir 566 with an increase in the applied force to transfer more load or force between the primary foot member 518 and the secondary foot member 522 during an increase in the load or force applied to the primary foot member 518. Conversely, the variable orifice 552 can decrease resistance to fluid flow during a decrease in the applied force to transfer less load or force between the primary foot member 518 and the secondary foot member 522 when the load factor on the primary foot member 518 decreases. Consequently, when a larger load is applied to the primary foot member 518, more energy is transferred from the primary foot member 518 to the secondary foot member 522 and the prosthetic foot device 510 can have a stiffer feel to the user. Conversely, when a smaller load is applied to the primary foot member 518, the variable orifice 552 allows more fluid to flow to the reservoir 566 so that more energy is absorbed by the enclosure 536 and less energy is transferred to the secondary foot member 522. Thus, the prosthetic foot device 510 can have a softer feel to the user under low load conditions.

Figure 8B:
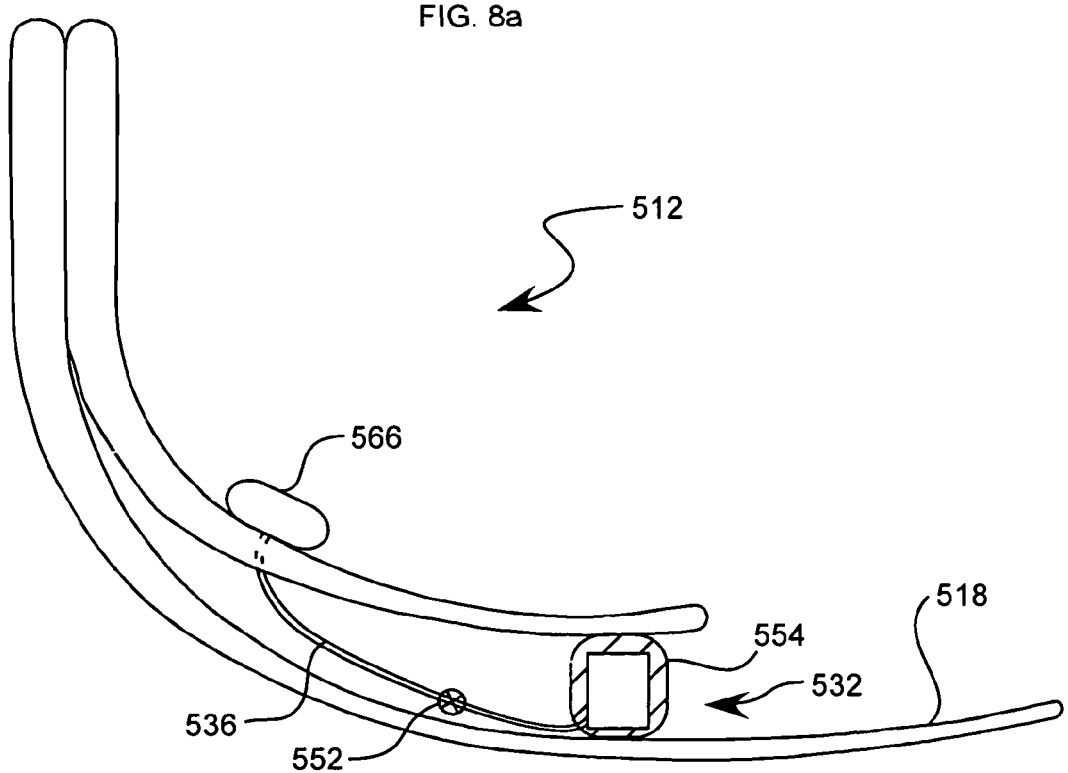
FIG. 8b is a side view of another prosthetic foot having an energy transfer mechanism or a variable resistance cell in accordance with another embodiment of the present invention.

The enclosure 532 can be formed by a chamber 554 and a piston 556 as shown in FIG. 8a, or a flexible bladder 562 as shown in FIG. 8b. The enclosure 532 can be compressible between the primary foot member 518 and the secondary foot member 522. Additionally, the enclosure 532 can be compressible between a first position in response to a relatively larger load and a second position in response to a relatively smaller load. The enclosure 532 in the first position can have a larger dimension, such as height, in which a lesser amount of the fluid passes through the variable orifice 552 into the reservoir 566. The enclosure 532 in the second position can have a smaller dimension, such as height, in which a greater amount of fluid passes through the variable orifice 552 into the reservoir 566.

Figure 9A:
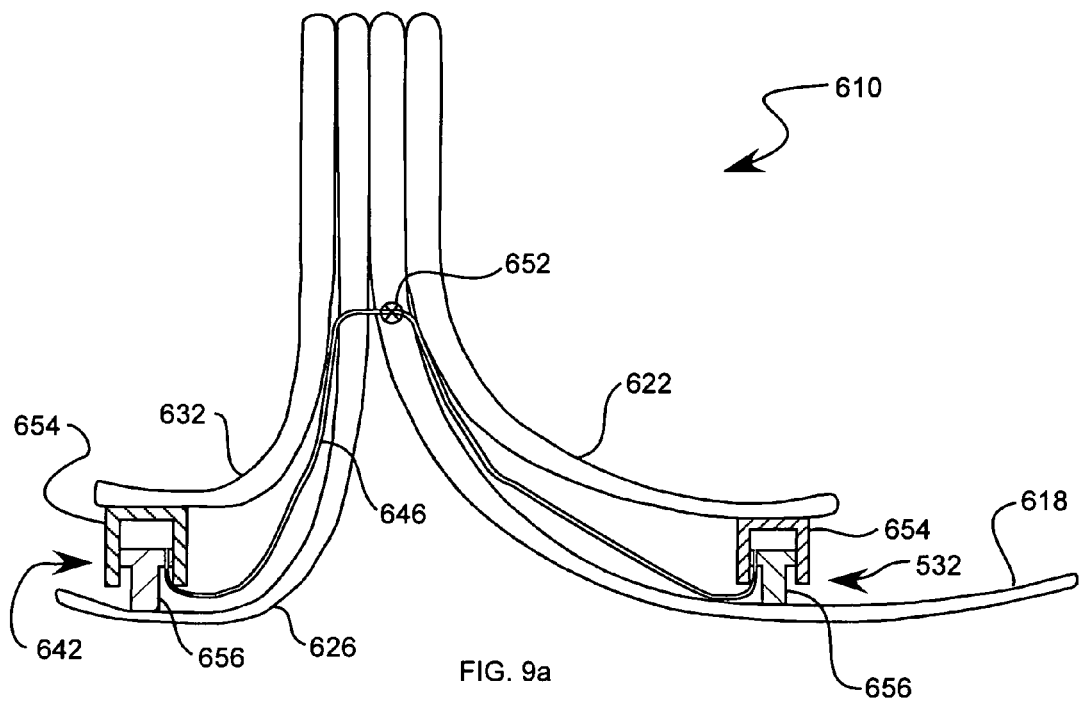
FIG. 9a is a side view of another prosthetic foot having an energy transfer mechanism or a variable resistance cell in accordance with another embodiment of the present invention.

Referring to FIGS. 9a and b, another prosthetic foot device 610 (FIG. 9a) or 612 (FIG. 9b) is shown which is similar in many respects to the foot devices described above. The foot device 610 can include a primary elongated forefoot member 618, a secondary forefoot member 622, a primary heel member 626, and a secondary heel member 632. The primary elongated foot member 618 can be attached to the stump of an amputee, and can extend therefrom to a toe location of a natural foot forming an elongated resilient spring that can store energy during deflection and resist forces applied to the primary elongated foot member 618. The secondary forefoot member 622 can also be an elongated resilient spring that can store energy during deflection. The secondary forefoot member 622 can also be coupled to the stump of an amputee, and/or the primary forefoot member 618, and can extend above the primary forefoot member.

The primary heel member 626 can also be coupled to the stump of an amputee, or attached to the primary forefoot member 618, and can extend therefrom to a heel location of a natural foot forming an elongated resilient spring that can store energy during deflection and resist forces applied to the primary heel member 626. The secondary heel member 632 can also be an elongated resilient spring that can store energy during deflection, and can be adjacent to and receive applied loads from the primary heel member 626. The secondary heel member 632 can be coupled to the stump of the amputee, the primary forefoot member 618, and/or the primary heel member 626, and can extend above the primary heel member.

The foot device 610 (or 612) can include a first enclosure 636, disposed between the primary forefoot member 618 and the secondary forefoot member 622, and a second enclosure 642 disposed between the primary heel member 626 and the secondary heel member 632. The first enclosure 636 and second enclosure 642 can be fluidly connected by a fluid path 646. A fluid can be disposed in the first and second enclosures 636 and 642 so that fluid can flow between the first and second enclosures 636 and 642 through the fluid path 646. Thus, the second enclosure can form a reservoir for the first enclosure, and the first enclosure can form a reservoir for the second enclosure. A variable orifice 652 can be operatively disposed in the fluid path 646 to provide variable resistance against fluid flow therethrough.

The variable orifice 652 can have a variable size to provide resistance against fluid flow through the fluid path 646, to variably transfer the applied force from the primary forefoot member 618 to the secondary forefoot member 622, and from the primary heel member 626 to the secondary heel member 632. The variable orifice 652 can variably transfer fluid between the first enclosure 636 and the second enclosure 642 during use. The variable orifice 652 can increase resistance to fluid flow between the first enclosure 636 and the second enclosure 642 with an increase in the applied force to transfer more load between the primary forefoot member 618 and secondary forefoot member 622, or the primary heel member 626 and the secondary heel member 632, during the increase in the applied force. The variable orifice 652 can also decrease resistance to fluid flow during a decrease in the applied force to transfer less load between the primary forefoot member 618 and the secondary forefoot member 622, or the primary heel member 626 and secondary heel member 632, during the decrease the applied force.

Figure 9B:
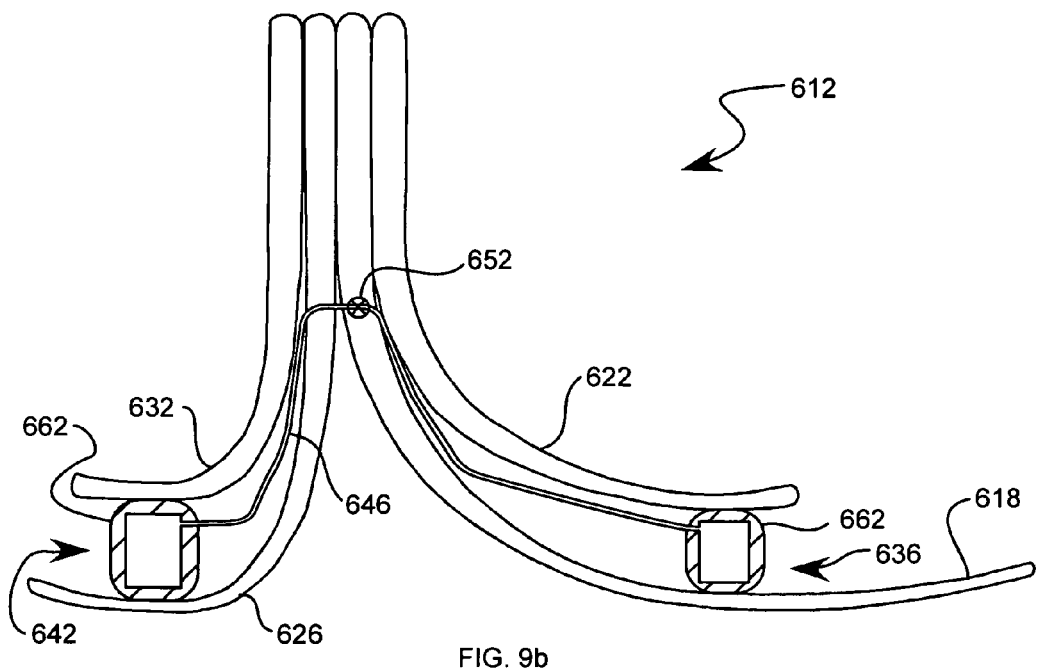
FIG. 9b is a side view of another prosthetic foot having an energy transfer mechanism or a variable resistance cell in accordance with another embodiment of the present invention.

The first and second enclosures 636 and 642 can each be formed by chambers 656 and pistons 656 as shown in FIG. 9*a*, or flexible bladders 662 as shown in FIG. 9*b*. The first enclosure 636 can be compressible between the primary foot member 618 and the secondary foot member 622. The second enclosure 642 can be compressible between the primary heel member 626 and the secondary heel member 632. Additionally, the first and second enclosures 636 and 642 can be compressible between a first position in response to a relatively larger load or force, and a second position in response to a relatively smaller load or force. The first and second enclosures 636 and 642 in the first position can have a larger dimension, such as height, in which a lesser amount of the fluid passes through the variable orifice 652. The first and second enclosures 636 and 642 in the second position can have a smaller dimension, such as height, in which a greater amount of fluid passes through the variable orifice 652.

Figure 10:
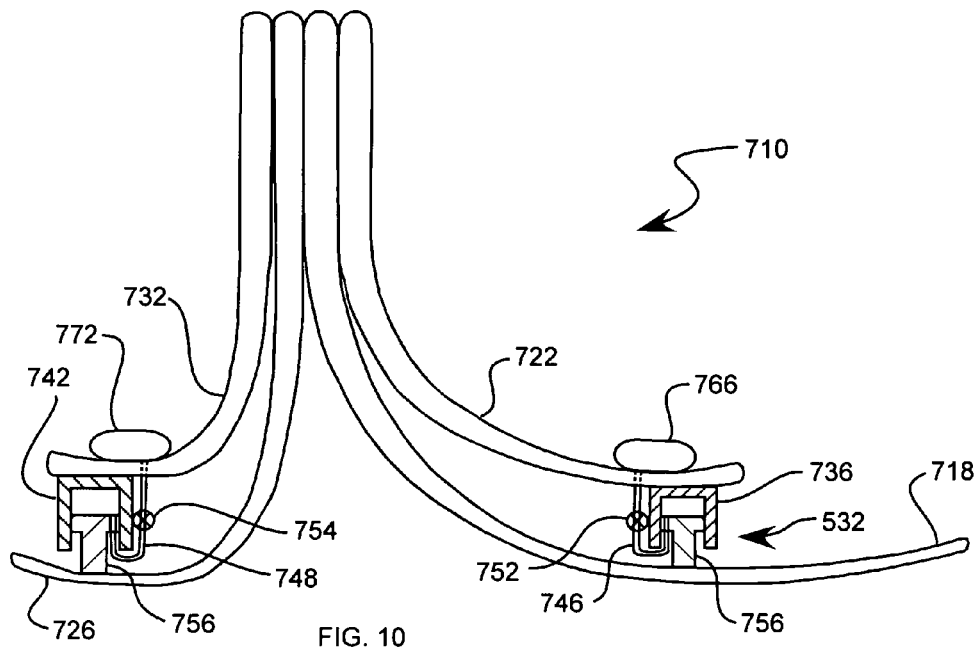
FIG. 10 is a side view of another prosthetic foot having an energy transfer mechanism or a variable resistance cell in accordance with another embodiment of the present invention.

Referring to FIG. 10, another prosthetic foot device 710 is shown which is similar in many respects to the foot devices described above. The foot device 710 can include a primary elongated forefoot member 718, a secondary forefoot member 722, a primary heel member 726, and a secondary heel member 732. The primary foot member 718 can be attached to the stump of an amputee, and extend therefrom to a toe location of a natural foot forming an elongated resilient spring that can store energy during deflection and resist forces applied to the primary elongated foot member 718. The secondary forefoot member 722 can be coupled to the stump of the amputee and/or the primary forefoot member, and can also be an elongated resilient spring that can store energy during deflection and can be adjacent to and receive applied loads from the primary forefoot member 718. The primary heel member 726 can also be attached to the stump of an amputee and/or the primary forefoot member 718, and can extend therefrom to a heel location of a natural foot forming an elongated resilient spring that can store energy during deflection and resist forces applied to the primary heel member 726. The secondary heel member 732 can be coupled to the stump of the amputee, the primary forefoot member and/or the primary heel member, and can also be an elongated resilient spring that can store energy during deflection, and can be adjacent to and receive applied loads from the primary heel member 726.

The foot device 710 can include a first enclosure 736, disposed between the primary forefoot member 718 and the secondary forefoot member 722, and a second enclosure 742 disposed between the primary heel member 726 and the secondary heel member 732. The first enclosure 736 can be fluidly connected to a first fluid path 746, and the second enclosure 742 can be fluidly connected to a second fluid path 748. The first fluid path 746 can also be connected to a first reservoir 766, and the second fluid path 748 can be connected to a second reservoir 772. A fluid can be disposed in the first and second enclosures 736 and 742 so that fluid can flow between the first and second enclosures 736 and 742 through the first and second fluid paths 746 and 748 to the first and second reservoirs 766 and 772, respectively. A first variable orifice 752 can be operatively disposed in the first fluid path 746 to provide variable resistance against fluid flow through the first fluid path 746. A second variable orifice 754 can be operatively disposed in the second fluid path 748 to provide variable resistance against fluid flow through the second fluid path 748.

The first and second variable orifices 752 and 754 can provide resistance against fluid flow through the first and second fluid paths 746 and 748, respectively, to variably transfer the applied force from the primary forefoot member 718 to the secondary forefoot member 722, and from the primary heel member 726 to the secondary heel member 732. The first variable orifice 752 can variably transfer fluid between the first enclosure 736 and the first reservoir 766 during use. The second variable orifice 754 can variably transfer fluid between the second enclosure 748 and the second reservoir during use 772. The use of two variable orifices, or different variable orifices for the forefoot and heel, allows the stiffness or feel of the forefoot and heel to be independently controlled or varied.

The first and second enclosures 736 and 742 can each be formed by chambers and pistons 756, as shown in FIG. 10, or flexible bladders as described above. The first enclosure 736 can be compressible between the primary foot member 718 and the secondary foot member 722. The second enclosure 742 can be compressible between the primary heel member 726 and the secondary heel member 732. Additionally, the first and second enclosures 736 and 742 can be compressible between a first position in response to a relatively larger load or applied force and a second position in response to a relatively smaller load or applied force. The first and second enclosures 736 and 742 in the first position can have a larger dimension, such as height, in which a lesser amount of the fluid passes through the first and second variable orifices 752 and 754. The first and second enclosures 736 and 742 in the second position can have a smaller dimension, such as height, in which a greater amount of fluid passes through the first and second variable orifices 752 and 754.

Figure 11:
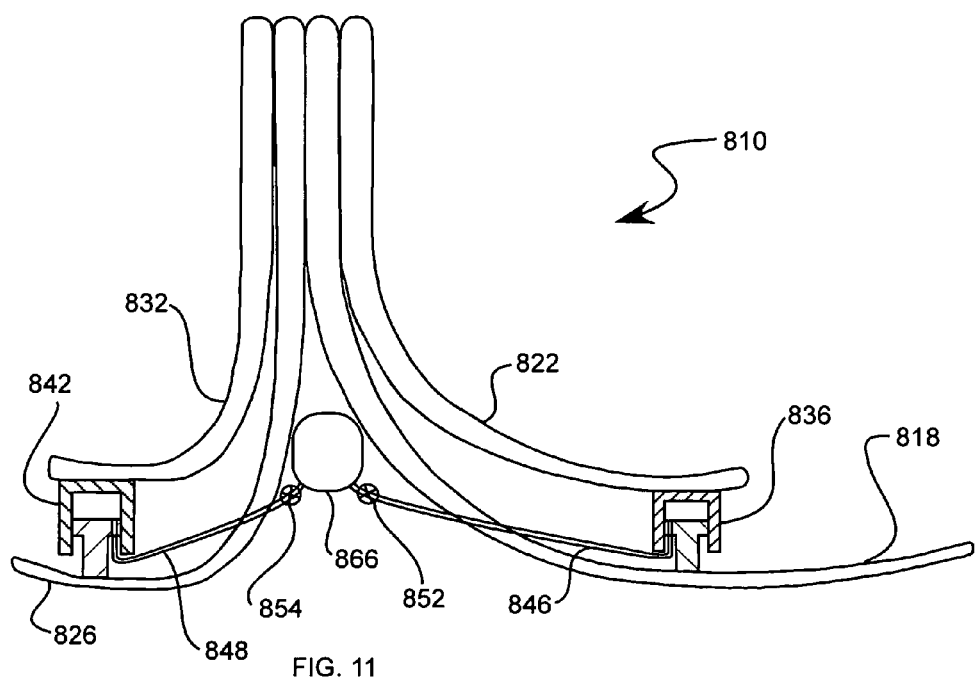
FIG. 11 is a side view of another prosthetic foot having an energy transfer mechanism or a variable resistance cell in accordance with another embodiment of the present invention.

Referring to FIG. 11, another prosthetic foot device 810 is shown which is similar in many respects to the foot devices described above. The foot device 810 can include a primary elongated forefoot member 818, a secondary forefoot member 822, a primary heel member 826, and a secondary heel member 832.

The foot device 810 can also include a first enclosure 836, disposed between the primary forefoot member 818 and the secondary forefoot member 822, and a second enclosure 842 disposed between the primary heel member 826 and the secondary heel member 832. The first enclosure 836 can be fluidly connected to a first fluid path 846, and the second enclosure 842 can be fluidly connected to a second fluid path 848. The first and second fluid paths 846 and 848 can also be connected to a reservoir 866. Thus, a single reservoir can be used. A fluid can be disposed in the first and second enclosures 836 and 842 so that fluid can flow between the first and second enclosures 836 and 842 through the first and second fluid paths 846 and 848 to the reservoir 866. A first variable orifice 852 can be operatively disposed in the first fluid path 846 to provide variable resistance against fluid flow through the first fluid path 846. A second variable orifice 854 can be operatively disposed in the second fluid path 848 to provide variable resistance against fluid flow through the second fluid path 848.

The first and second variable orifices 852 and 854 can provide resistance against fluid flow through the first and second fluid paths 846 and 848, respectively, to variably transfer the applied force from the primary forefoot member 818 to the secondary forefoot member 822, and from the primary heel member 826 to the secondary heel member 832. The first variable orifice 852 can variably transfer fluid between the first enclosure 836 and the reservoir 866 during use. The second variable orifice 754 can variably transfer fluid between the second enclosure 748 and the reservoir 866 during use.

Figure 12:
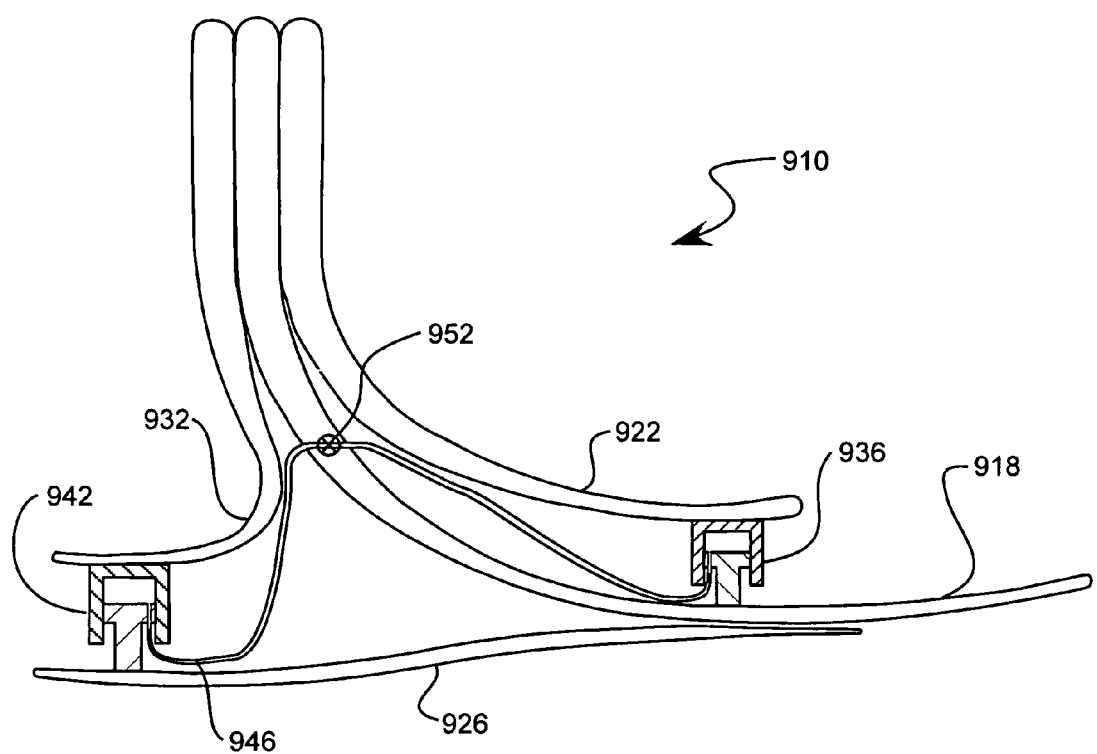
FIG. 12 is a side view of another prosthetic foot having an energy transfer mechanism or a variable resistance cell in accordance with another embodiment of the present invention.

Referring to FIG. 12, another prosthetic foot device 910 is shown which is similar in many respects to the foot devices described above. The foot device 910 can include a primary elongated forefoot member 918, a secondary forefoot member 922, a primary heel member or foot plate 926, and a secondary heel member 932. The primary foot member 918 can be attached to the stump of an amputee, and extend therefrom to a toe location of a natural foot forming an elongated resilient spring that can store energy during deflection and resist forces applied to the primary elongated foot member 918. The secondary forefoot member 922 can be coupled to the stump of the amputee and/or the primary forefoot member, and can also be an elongated resilient spring that can store energy during deflection and can be adjacent to and receive applied loads from the primary forefoot member 918. The primary heel member 926 can extend from a heel location of a natural heel to the primary forefoot member 918, and can also be an elongated resilient spring that can store energy during deflection. The secondary heel member 932 can be coupled to the stump of the amputee, the primary forefoot member and/or the primary heel member, and can also be an elongated resilient spring that can store energy during deflection, and can be adjacent to and receive applied loads from the primary heel member 926. The various members 918, 922, 926 and 932 can be resilient and energy storing foot members that deflect or flex, storing energy, and can be formed of a fiber reinforced resin material, such as a graphite-reinforced resin.

The foot device 910 can include a first enclosure 936, disposed between the primary forefoot member 918 and the secondary forefoot member 922, and a second enclosure 942 disposed between the primary heel member 926 and the secondary heel member 932. The first enclosure 936 and second enclosure 942 can be fluidly connected by a fluid path 946. A fluid can be disposed in the first and second enclosures 936 and 942 so that fluid can flow between the first and second enclosures 936 and 942 through the fluid path 946. A variable orifice 952 can be operatively disposed in the fluid path 946 to provide variable resistance against fluid flow therethrough.

The variable orifice 952 can have a variable size to provide resistance against fluid flow through the fluid path 946, to variably transfer the applied force from the primary forefoot member 918 to the secondary forefoot member 922, and from the primary heel member 926 to both the secondary heel member 932 and the primary foot member 918. The variable orifice 952 can variably transfer fluid between the first enclosure 936 and the second enclosure 942 during use. The variable orifice 952 can increase resistance to fluid flow between the first enclosure 936 and the second enclosure 942 with an increase in the applied force to transfer more load between the primary forefoot member 918 and secondary forefoot member 922, or the primary heel member 926 and the secondary heel member 932, during the increase in the applied force. The variable orifice 952 can also decrease resistance to fluid flow during a decrease in the applied force to transfer less load between the primary forefoot member 918 and the secondary forefoot member 922, or the primary heel member 926 and secondary heel member 932, during the decrease the applied force.

The first and second enclosures 936 and 942 can each be formed by chambers and pistons 956, as shown in FIG. 12, or flexible bladders as described above. The first enclosure 936 can be compressible between the primary foot member 918 and the secondary foot member 922. The second enclosure 942 can be compressible between the primary heel member 926 and the secondary heel member 932. Additionally, the first and second enclosures 936 and 942 can be compressible between a first position in response to a relatively larger load or applied force and a second position in response to a relatively smaller load or applied force. The first and second enclosures 936 and 942 in the first position can have a larger dimension, such as height, in which a lesser amount of the fluid passes through the variable orifice 952. The first and second enclosures 936 and 942 in the second position can have a smaller dimension, such as height, in which a greater amount of fluid passes through the variable orifice 952.

Alternatively, the first and second enclosures 936 and 942 can have separate first and second reservoirs and separate first and second variable orifices.

Figure 13:
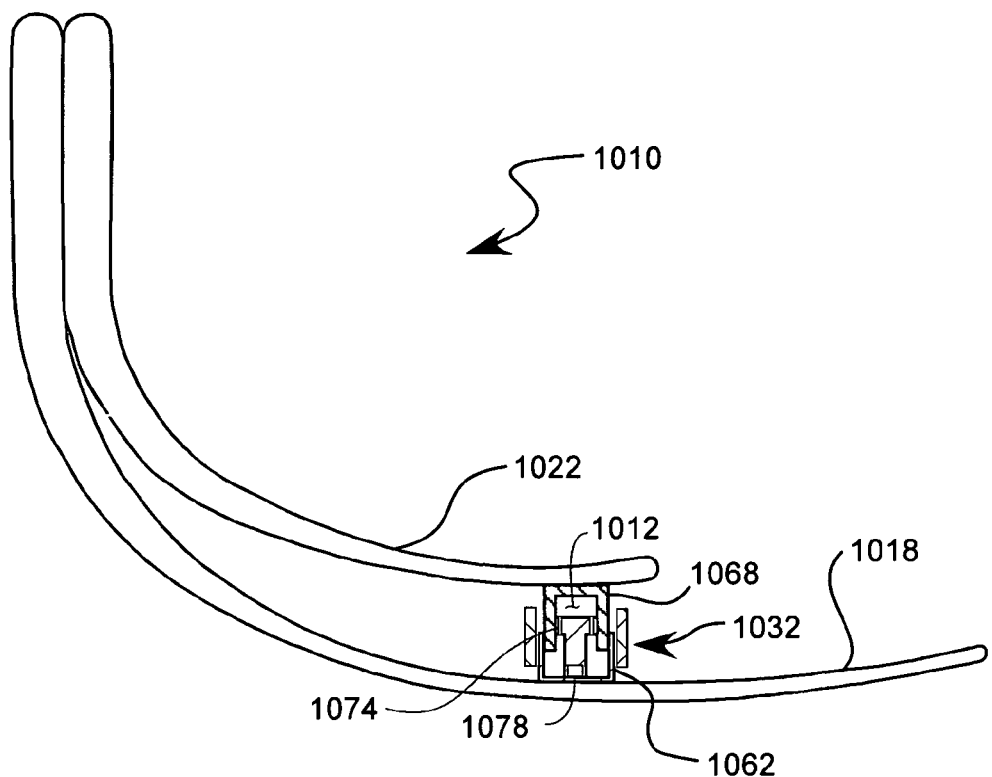
FIG. 13 is a side view of another prosthetic foot having an energy transfer mechanism or a variable resistance cell in accordance with another embodiment of the present invention.

Referring to FIG. 13, another prosthetic foot device 1010 is shown which is similar in many respects to those described above. The foot device 1010 can include a primary elongated foot or forefoot member 1018 and a secondary foot or reinforcement member 1022. The primary elongated foot member 1018 can be attached to the stump of an amputee, and can extend therefrom to a toe location of a natural toe, and can form an elongated resilient spring that can store energy during deflection and resist forces applied to the primary foot member 1018. The secondary foot member 1022 can also be an elongated resilient spring that can store energy during deflection and can be adjacent to and receive applied loads from the primary foot member 1018. For example, the secondary foot or reinforcement member 1022 can be attached to the stump of an amputee and/or coupled to the primary foot member, and can extend above the primary foot member, as shown.

The foot device can include means for variably transferring energy between the primary foot member 1018 and the secondary foot member 1022 during use. The means for variably transferring energy can increase resistance against the forces applied to the primary foot member 1018 when the forces increase so that more load can be transferred between the primary foot member 1018 and the secondary foot member 1022. The means for variably transferring energy can also decrease resistance against the forces applied to the primary foot member 1018 when the forces decrease so that less load is transferred between the primary foot member 1018 and the secondary foot member 1022.

The means for variably transferring energy can be disposed between the primary elongated foot member 1018 and the secondary foot member 1022, and can include variable resistance cell 1032 disposed between the primary foot member 1018 and the secondary foot member 1022. The variable resistance cell can include a chamber 1068 associated with one of the primary or secondary foot members.

A piston 1064 can be associated with another of the primary 1018 and secondary foot 1022 members. The piston 1064 can be movable in the chamber 1068. The piston 1064 and chamber 1068 can define a volume that changes in response to the load factor. At least one aperture 1074 can be formed through the piston and in communication with the chamber. The chamber and the piston can be displaceable with respect to one another between the first and second foot members.

A variable viscosity fluid 1012 can be disposed in the chamber 1068 and can be displaceable through the at least one aperture 1074 in the piston 1064 in response to the load factor. The variable viscosity fluid can remain between the first and second foot members. The variable viscosity fluid 1012 can have a viscosity that is variable corresponding to the load factor to vary an ability of the variable viscosity fluid to flow through the at least one aperture.

Figure 14:
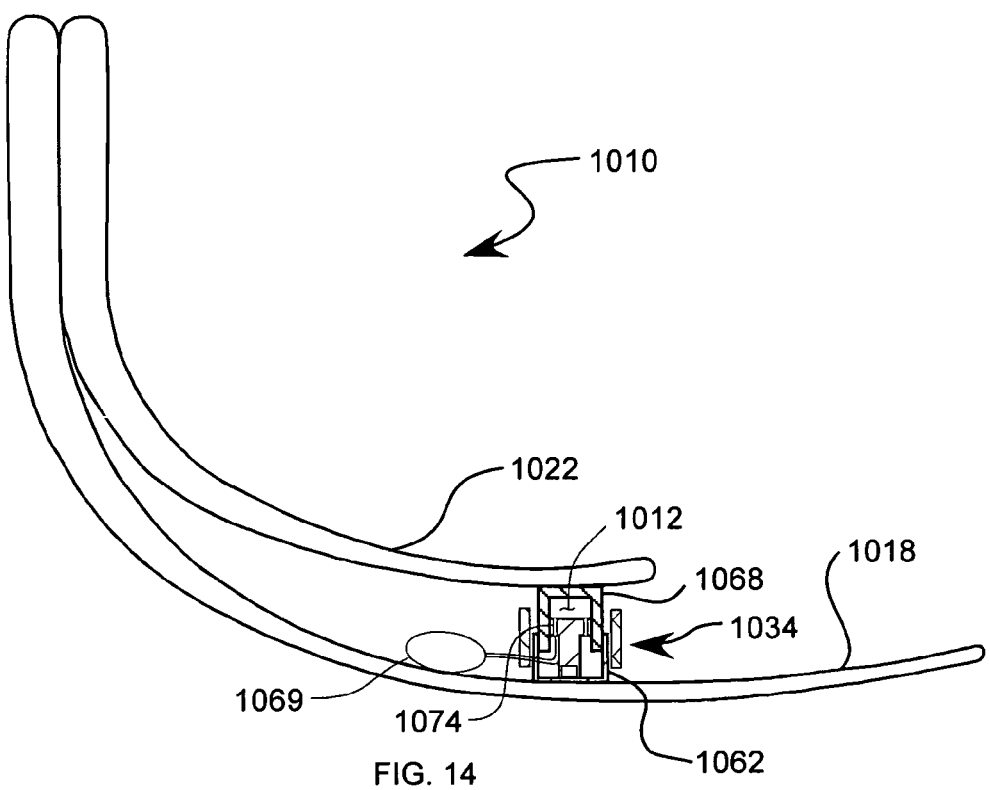
FIG. 14 is a side view of another prosthetic foot having an energy transfer mechanism or a variable resistance cell in accordance with another embodiment of the present invention.

The cell 1032 can also include a reservoir 1062 that can receive variable viscosity fluid from the chamber 1068 through the aperture 1074. In one aspect, the reservoir 1062 can be a flexible enclosure that can expand as fluid enters the reservoir. In another aspect, the reservoir 1062 can include a separate enclosure 1069 such as a flexible bladder, as shown in FIG. 14.

The chamber 1068 can be compressible between the primary foot member 1018 and the secondary foot member 1022. Additionally, the chamber 1068 can be compressible between a first position in response to a relatively larger load and a second position in response to a relatively smaller load. The chamber 1068 in the first position can have a larger dimension, such as height, in which a lesser amount of the fluid passes through the aperture 1074 into the reservoir 1062. The chamber 1068 in the second position can have a smaller dimension, such as height, in which a greater amount of fluid passes through the aperture 1074 into the reservoir 1062.

The variable viscosity fluid 1012 can include a magneto rheologic fluid responsive to a magnetic field, an electro rheologic fluid responsive to an electric field, or combinations of magneto and electro rheologic fluids. Additionally, the variable viscosity fluid 1012 can also include a shear stiffening material that increases in viscosity with an increase in the load factor applied to the shear stiffening material.

The load factor can include at least one load factor from a load, a load rate, a load acceleration, a strain, a strain rate, a strain acceleration, a pressure, a pressure rate, a pressure acceleration, a deflection, a deflection rate, and a deflection acceleration.

The cell 1032 can also include a transducer 1078 to sense a load factor, and a power source 1080, coupled to the transducer to power the variable viscosity fluid 1012. Control electronics (not shown) can be coupled to the transducer 1078 and the variable viscosity fluid 1012 in order to apply an electric or magnetic field in response to the load factor sensed by the transducer. The control electronics can be programmable, and the power source can include a generator.

The cell thus described in FIGS. 13-14 can also be used with the feet described above.

Figure 15:
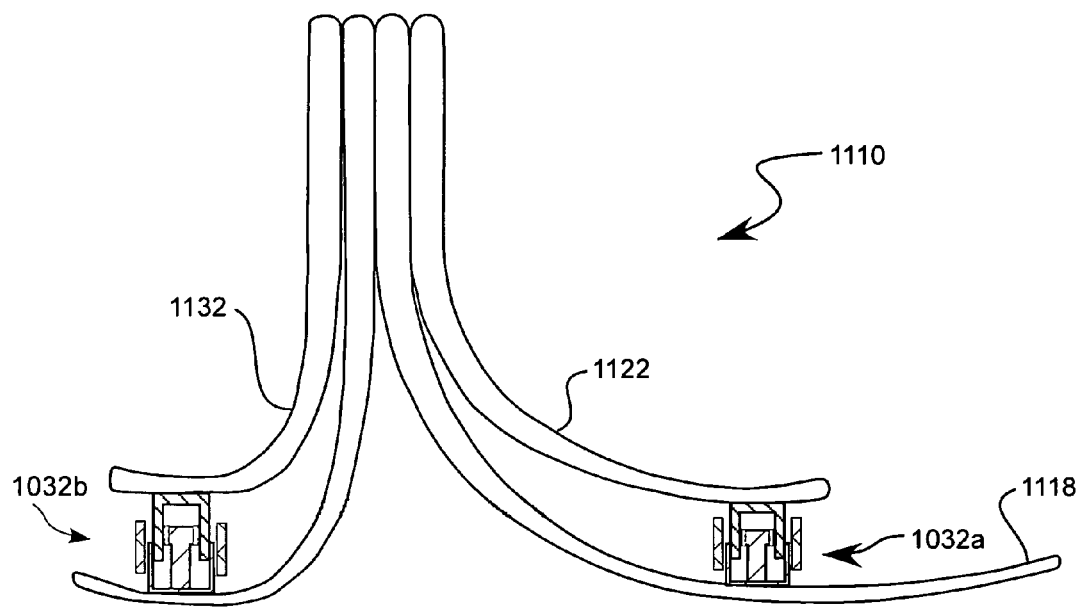
FIG. 15 is a side view of another prosthetic foot having an energy transfer mechanism or a variable resistance cell in accordance with another embodiment of the present invention.

Referring to FIG. 15, another prosthetic foot device 1110 is shown which is similar in many respects to the foot devices described above. The foot device 1110 can include a primary elongated forefoot member 1118, a secondary forefoot member 1122, a primary heel member 1126, and a secondary heel member 1132. The primary elongated foot member 1118 can be attached to the stump of an amputee, and can extend therefrom to a toe location of a natural foot forming an elongated resilient spring that can store energy during deflection and resist forces applied to the primary elongated foot member 1118. The secondary forefoot member 1122 can also be an elongated resilient spring that can store energy during deflection. The secondary forefoot member 1122 can also be coupled to the stump of an amputee, and/or the primary forefoot member 1118, and can extend above the primary forefoot member.

The primary heel member 1126 can also be coupled to the stump of an amputee, or attached to the primary forefoot member 1118, and can extend therefrom to a heel location of a natural foot forming an elongated resilient spring that can store energy during deflection and resist forces applied to the primary heel member 1126. The secondary heel member 1132 can also be an elongated resilient spring that can store energy during deflection, and can be adjacent to and receive applied loads from the primary heel member 1126. The secondary heel member 632 can be coupled to the stump of the amputee, the primary forefoot member 1118, and/or the primary heel member 1126, and can extend above the primary heel member.

The foot device 1110 can include a first variable resistance cell 1032*a*, disposed between the primary forefoot member 1118 and the secondary forefoot member 1122, and a second variable resistance cell 1032*b* disposed between the primary heel member 1126 and the secondary heel member 1132. The first cell 1032*a* and second cell 1032*b* can be similar in structure and function to the cell 1032 described above and shown in FIGS. 13 and 14.

Figure 16:
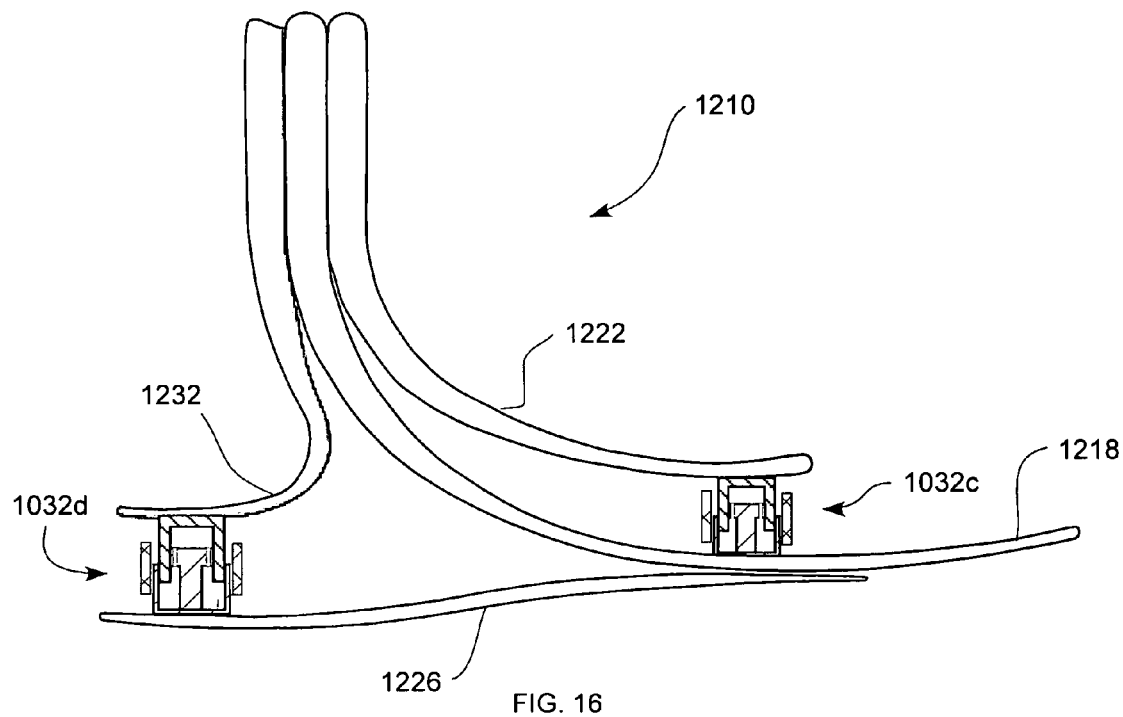
FIG. 16 is a side view of another prosthetic foot having an energy transfer mechanism or a variable resistance cell in accordance with another embodiment of the present invention.

Referring to FIG. 16, another prosthetic foot device 1210 is shown which is similar in many respects to the foot devices described above. The foot device 1210 can include a primary elongated forefoot member 1218, a secondary forefoot member 1222, a primary heel member or foot plate 1226, and a secondary heel member 1232. The primary foot member 1218 can be attached to the stump of an amputee, and extend therefrom to a toe location of a natural foot forming an elongated resilient spring that can store energy during deflection and resist forces applied to the primary elongated foot member 1218. The secondary forefoot member 1222 can be coupled to the stump of the amputee and/or the primary forefoot member, and can also be an elongated resilient spring that can store energy during deflection and can be adjacent to and receive applied loads from the primary forefoot member 1218. The primary heel member 1226 can extend from a heel location of a natural heel to the primary forefoot member 1218, and can also be an elongated resilient spring that can store energy during deflection. The secondary heel member 1232 can be coupled to the stump of the amputee, the primary forefoot member and/or the primary heel member, and can also be an elongated resilient spring that can store energy during deflection, and can be adjacent to and receive applied loads from the primary heel member 1226. The various members 1218, 1222, 1226 and 1232 can be resilient and energy storing foot members that deflect or flex, storing energy, and can be formed of a fiber reinforced resin material, such as a graphite-reinforced resin.

The foot device 1210 can include a first variable resistance cell 1032c, disposed between the primary forefoot member 1218 and the secondary forefoot member 1222, and a second variable resistance cell 1032d disposed between the primary heel member 1226 and the secondary heel member 1232. The first cell 1032c and second cell 1032d can be similar in structure and function to the cell 1032 described above and shown in FIGS. 13 and 14.

Figure 17:
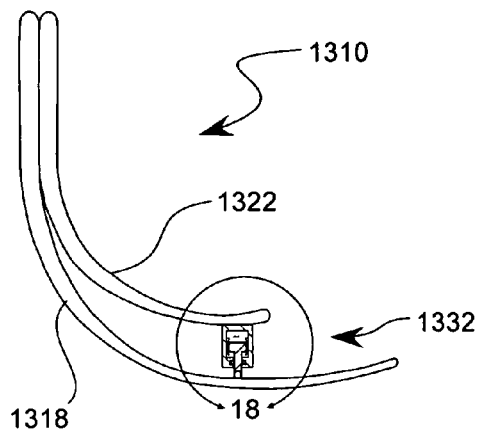
FIG. 17 is a side view of another prosthetic foot having an energy transfer mechanism or a variable resistance cell in accordance with another embodiment of the present invention.
Figure 18:
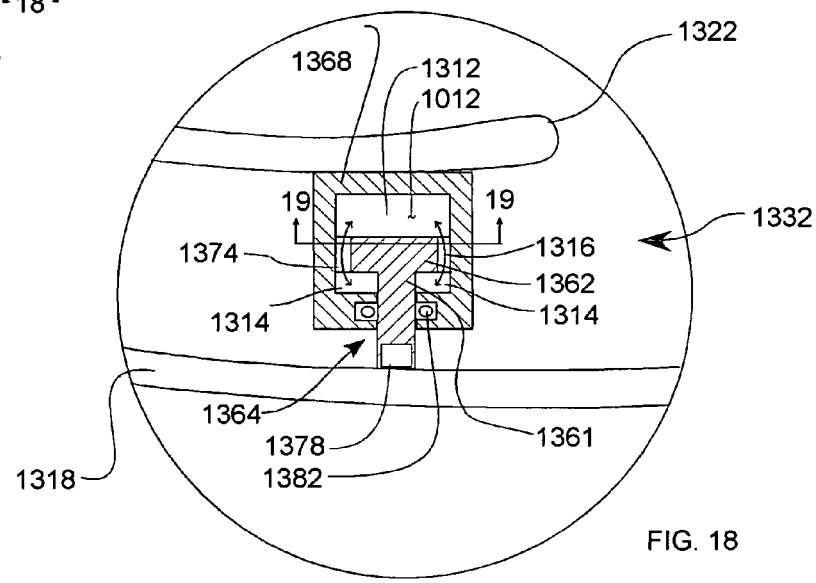
FIG. 18 is a fragmentary side view of the prosthetic foot and energy transfer mechanism of FIG. 17.
Figure 19:
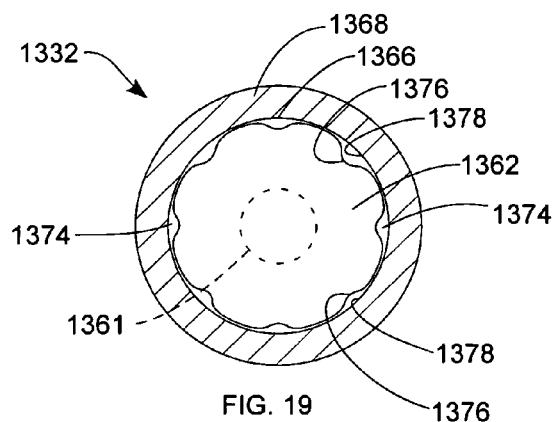
FIG. 19 is a cross section of a piston of the energy transfer mechanism of the prosthetic foot of FIG. 17.

Referring to FIG. 17-19, another prosthetic foot device 1310 is shown which is similar in many respects to the foot devices described above. The foot device 1310 can include a primary elongated forefoot member 1318, and a secondary forefoot member 1322. The primary foot member 1318 can be attached to the stump of an amputee, and extend therefrom to a toe location of a natural foot forming an elongated resilient spring that can store energy during deflection and resist forces applied to the primary elongated foot member 1318. The secondary forefoot member 1322 can be coupled to the stump of the amputee and/or the primary forefoot member, and can also be an elongated resilient spring that can store energy during deflection and can be adjacent to and receive applied loads from the primary forefoot member 1318. Although not shown, it will be appreciated that the prosthetic foot device 1310 can also include heel members, as described above. The various members 1318, 1322, and heel members if present, can be resilient and energy storing foot members that deflect or flex, storing energy, and can be formed of a fiber reinforced resin material, such as a graphite-reinforced resin.

The foot device can include means for variably transferring energy between the primary foot member 1318 and the secondary foot member 1322 during use. The means for variably transferring energy can increase resistance against the forces applied to the primary foot member 1318 when the forces increase so that more load can be transferred between the primary foot member 1318 and the secondary foot member 1322. The means for variably transferring energy can also decrease resistance against the forces applied to the primary foot member 1318 when the forces decrease so that less load is transferred between the primary foot member 1318 and the secondary foot member 1322.

The means for variably transferring energy can be disposed between the primary elongated foot member 1318 and the secondary foot member 1322, and can include variable resistance cell 1332 disposed between the primary foot member 1318 and the secondary foot member 1322. The variable resistance cell can include a chamber 1368 associated with one of the primary or secondary foot members. A piston 1364 can be associated with the other of the primary 1318 and secondary foot 1322 members. The piston 1364 can be movable within the chamber 1368, such that the chamber and the piston can be displaceable with respect to one another between the first and second foot members.

Thus, the chamber 1368 can substantially enclose the piston 1364, or a piston head 1362, and a rod 1361 coupled to the piston head can extend out of the chamber. An o-ring 1382 can form a seal between the rod and the chamber to prevent or reduce leakage of fluid from within the chamber.

The piston 1364 inside the chamber 1368 can define a first variable space 1312 and a second variable space 1314 within the chamber. The first and second spaces 1312 and 1314 can be separated by the piston such that the two spaces can be on opposite sides of the piston. In this way, the volume of the spaces can vary or change as the piston is moved within the chamber in response to the load factor.

At least one aperture or passage 1374 can be formed between the piston 1364 and the chamber 1368. In one aspect, the aperture 1374 can be formed between a piston head 1362 of the piston 1364 and a wall 1366 of the chamber 1368. The aperture 1374 can include a channel formed in one of the piston head 1362 or wall 1366 of the chamber and a mating surface in the other of the piston head or wall of the chamber. Thus, as shown in FIG. 19, the aperture can include a channel 1376 formed in the piston head 1362 and a mating surface 1378 formed in the wall 1366 of the chamber. Advantageously, the aperture 1374 formed between the head 1362 of the piston 1364 and a wall 1366 of the chamber 1368 can allow fluid to flow within the chamber 1368 between spaces 1312 and 1314 positioned on opposite sides of the piston head 1362, as indicated by an arrow at 1316.

In another aspect, the channel (not shown) can be formed in the wall 1366 of the chamber 1368 and the mating surface (not shown) can be on the piston head 1362. In yet another aspect, the piston 1364 and chamber 1368 of the variable resistance cell 1332 can have a plurality of channels and mating surfaces with some of the channels formed in the piston head and some formed in the wall of the chamber. Other configurations of channels and mating surfaces are also possible so long as the aperture formed between the channel and mating surface allows fluid to flow through the aperture between the spaces on opposite sides of the piston head.

Referring again to FIGS. 17-19, a variable viscosity fluid 1012 can be disposed in the chamber 1368 and can be displaceable between the two spaces 1312 and 1314 through the aperture 1374 between the piston 1364 and the chamber 1368 in response to the load factor. In this way, the variable viscosity fluid 1012 can remain between the first and second foot members without requiring a separate reservoir from the chamber. The variable viscosity fluid 1012 can have a viscosity that is variable corresponding to the load factor to vary an ability of the variable viscosity fluid to flow through the at least one aperture.

The piston 1364 can be movable in the chamber 1368 between the primary foot member 1318 and the secondary foot member 1322. Additionally, the piston 1364 can be movable in the chamber 1368 between a first position in response to a relatively larger load and a second position in response to a relatively smaller load. In the first position the first space 1312 can have a larger dimension, such as volume, in which a lesser amount of the fluid passes through the aperture 1374 into the second space 1314. In the second position the first space 1312 can have a smaller dimension, such as volume, in which a greater amount of fluid passes through the aperture 1374 into the second space 1314.

The variable viscosity fluid 1012 can include a magneto rheologic fluid responsive to a magnetic field, an electro rheologic fluid responsive to an electric field, or combinations of magneto and electro rheologic fluids. Additionally, the variable viscosity fluid 1012 can also include a shear stiffening material that increases in viscosity with an increase in the load factor applied to the shear stiffening material.

The load factor can include at least one load factor from a load, a load rate, a load acceleration, a strain, a strain rate, a strain acceleration, a pressure, a pressure rate, a pressure acceleration, a deflection, a deflection rate, and a deflection acceleration.

The cell 1332 can also include a transducer 1378 to sense a load factor, and a power source (not shown), coupled to the transducer to power the variable viscosity fluid 1012. Control electronics (not shown) can be coupled to the transducer 1378 and the variable viscosity fluid 1012 in order to apply an electric or magnetic field in response to the load factor sensed by the transducer. The control electronics can be programmable, and the power source can include a generator.

Figure 20:
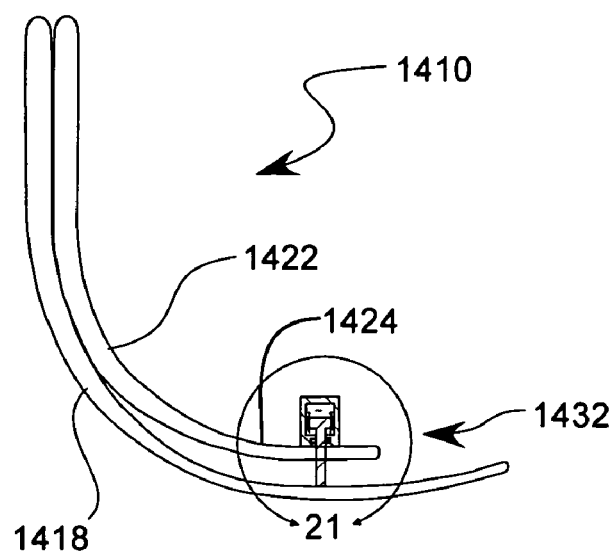
FIG. 20 is a side view of another prosthetic foot having an energy transfer mechanism or a variable resistance cell in accordance with another embodiment of the present invention.
Figure 21:
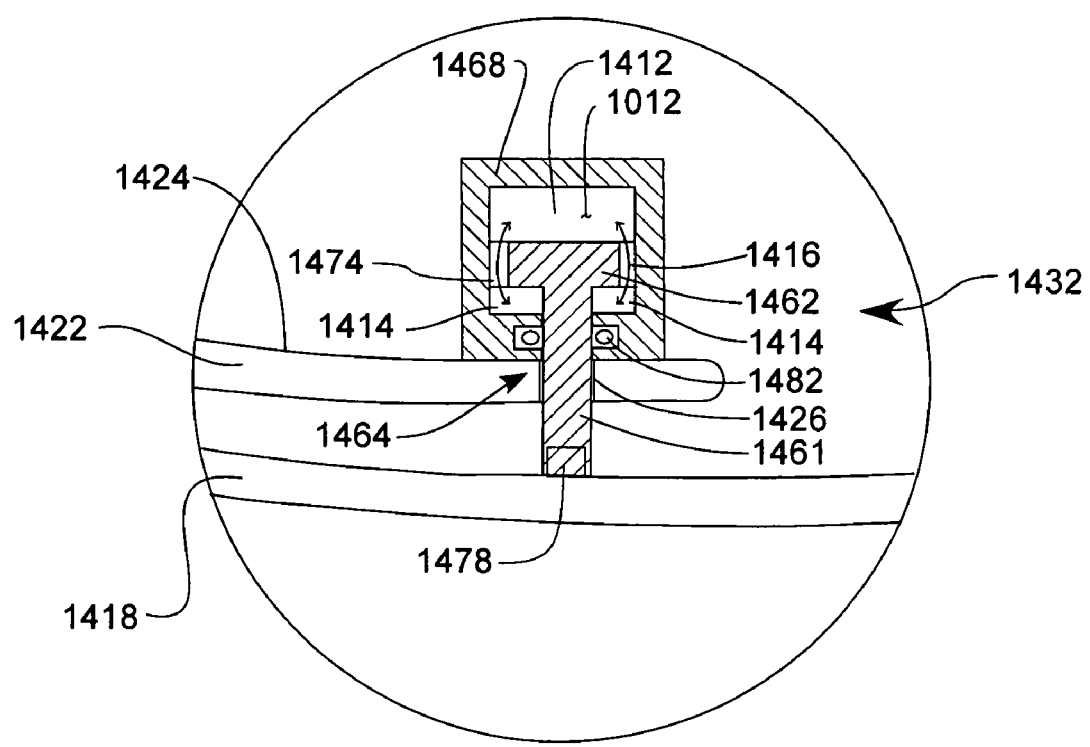
FIG. 21 is a fragmentary side view of the prosthetic foot and energy transfer mechanism of FIG. 20.

As illustrated in FIGS. 20-21, another prosthetic foot device 1410 is shown which is similar in many respects to the foot devices described above. The foot device 1410 can include a primary elongated forefoot member 1418, and a secondary forefoot member 1422. The primary foot member 1418 can be attached to the stump of an amputee, and extend therefrom to a toe location of a natural foot forming an elongated resilient spring that can store energy during deflection and resist forces applied to the primary elongated foot member 1418. The secondary forefoot member 1422 can be coupled to the stump of the amputee and/or the primary forefoot member, and can also be an elongated resilient spring that can store energy during deflection and can be adjacent to and receive applied loads from the primary forefoot member 1418. Although not shown, it will be appreciated that the prosthetic foot device 1410 can also include heel members, as described above. The various members 1418, 1422, and heel members if present, can be resilient and energy storing foot members that deflect or flex, storing energy, and can be formed of a fiber reinforced resin material, such as a graphite-reinforced resin.

The foot device can include means for variably transferring energy between the primary foot member 1418 and the secondary foot member 1422 during use. The means for variably transferring energy can increase resistance against the forces applied to the primary foot member 1418 when the forces increase so that more load can be transferred between the primary foot member 1418 and the secondary foot member 1422. The means for variably transferring energy can also decrease resistance against the forces applied to the primary foot member 1418 when the forces decrease so that less load is transferred between the primary foot member 1418 and the secondary foot member 1422.

The means for variably transferring energy can be associated with the primary elongated foot member 1418 and the secondary foot member 1422 to transfer energy between the primary elongated foot member and the secondary foot member. For example, the means for variably transferring energy can include variable resistance cell, indicated generally at 1432. The variable resistance cell 1432 can include a chamber 1468 disposed on a top surface 1424 of the secondary foot member 1422. A piston 1464 can be coupled to the primary foot member 1418. The piston 1464 can have a piston rod 1461 that can extend through an aperture 1426 in the secondary foot member 1422 to a piston head 1462 that can be movable within a chamber 1468, such that the chamber and the piston can be displaceable with respect to one another between the first and second foot members.

Advantageously, with the chamber 1468 disposed on the top surface 1424 of the secondary foot member 1422 the primary foot member 1418 and the secondary foot member 1422 can be spaced closer together such that the primary foot member can engage the secondary foot member sooner during the user's gait Additionally, the closer spacing of the primary foot member 1418 and secondary foot member 1422 reduces the length of the piston rod 1461 and the stroke of the piston head 1462 in the chamber 1468 as the primary foot member 1418 is displaced toward the secondary foot member 1422. In this way, the piston rod 1461, piston head 1462 and chamber 1468 can be reduced in size while maintaining the advantages of the variable resistance cells described in the embodiments above.

Thus, the chamber 1468 can substantially enclose the piston head 1462, and the piston rod 1461 coupled to the piston head can extend out of the chamber and through the aperture 1426 in the secondary foot member 1422. An o-ring 1482 can form a seal between the rod and the chamber to prevent or reduce leakage of fluid from within the chamber.

The piston head 1462 inside the chamber 1468 can define a first variable space 1412 and a second variable space 1414 within the chamber. The first and second variable spaces 1412 and 1414 can be separated by the piston head 1462 such that the two spaces can be on opposite sides of the piston head. In this way, the volume of the spaces can vary or change as the piston head is moved within the chamber in response to the load factor.

At least one aperture or passage 1474 can be formed between the piston head 1462 and the chamber 1468. In one aspect, the aperture 1474 can be formed between the piston head 1462 and a wall 1466 of the chamber 1468. The aperture 1474 can include a channel formed in one of the piston head 1462 or wall 1466 of the chamber and a mating surface in the other of the piston head or wall of the chamber. Advantageously, the aperture 1474 formed between the piston head 1462 and a wall 1466 of the chamber 1468 can allow fluid to flow within the chamber 1468 between spaces 1412 and 1414 positioned on opposite sides of the piston head 1462, as indicated by the arrow at 1416.

As described in the embodiments above, a variable viscosity fluid 1012 can be disposed in the chamber 1468 and can be displaceable between the two spaces 1412 and 1414 through the aperture 1474 between the piston 1464 and the chamber 1468 in response to the load factor. The variable viscosity fluid 1012 can have a viscosity that is variable corresponding to the load factor to vary an ability of the variable viscosity fluid to flow through the at least one aperture. The piston 1464 can be movable in the chamber 1468 between a first position in response to a relatively larger load in which a lesser amount of the fluid passes through the aperture 1474, and a second position in response to a relatively smaller load in which a greater amount of fluid passes through the aperture 1474 into the second space 1414. The variable viscosity fluid 1012 can include a magneto rheologic fluid responsive to a magnetic field, an electro rheologic fluid responsive to an electric field, or combinations of magneto and electro rheologic fluids as well as shear stiffening materials that increase in viscosity with an increase in the load factor applied to the shear stiffening material.

The cell 1432 can also include a transducer 1478 to sense a load factor, and a power source (not shown), coupled to the transducer to power the variable viscosity fluid 1012. Control electronics (not shown) can be coupled to the transducer 1478 and the variable viscosity fluid 1012 in order to apply an electric or magnetic field in response to the load factor sensed by the transducer. The control electronics can be programmable, and the power source can include a generator.

Figure 22:
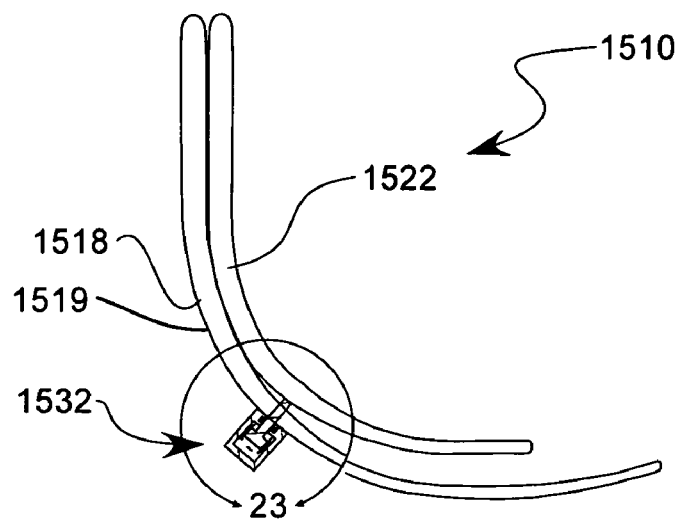
FIG. 22 is a side view of another prosthetic foot having an energy transfer mechanism or a variable resistance cell in accordance with another embodiment of the present invention.
Figure 23:
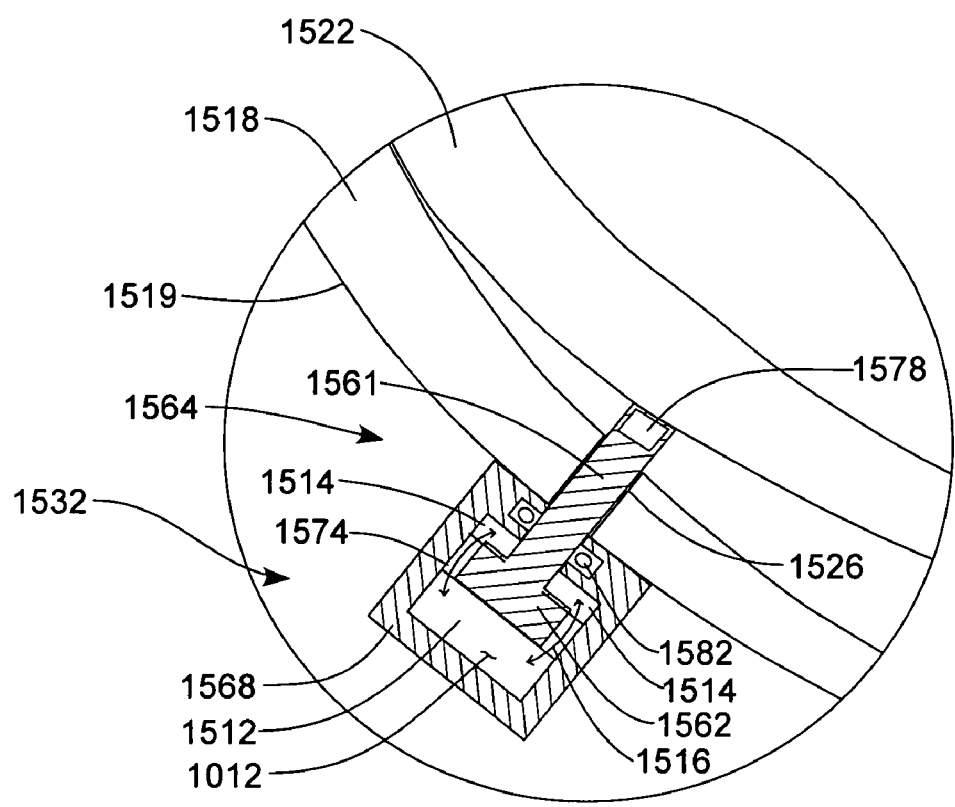
FIG. 23 is a fragmentary side view of the prosthetic foot and energy transfer mechanism of FIG. 22.

As illustrated in FIGS. 22-23, another prosthetic foot device 1510 is shown which is similar in many respects to the foot devices described above. The foot device 1510 can include a primary elongated forefoot member 1518, and a secondary forefoot member 1522. The primary foot member 1518 can be attached to the stump of an amputee, and extend therefrom to a toe location of a natural foot forming an elongated resilient spring that can store energy during deflection and resist forces applied to the primary elongated foot member 1518. The secondary forefoot member 1522 can be coupled to the stump of the amputee and/or the primary forefoot member, and can also be an elongated resilient spring that can store energy during deflection and can be adjacent to and receive applied loads from the primary forefoot member 1518. Although not shown, it will be appreciated that the prosthetic foot device 1510 can also include heel members, as described above. The various members 1518, 1522, and heel members if present, can be resilient and energy storing foot members that deflect or flex, storing energy, and can be formed of a fiber reinforced resin material, such as a graphite-reinforced resin.

The foot device can include means for variably transferring energy between the primary foot member 1518 and the secondary foot member 1522 during use. The means for variably transferring energy can increase resistance against the forces applied to the primary foot member 1518 when the forces increase so that more load can be transferred between the primary foot member 1518 and the secondary foot member 1522. The means for variably transferring energy can also decrease resistance against the forces applied to the primary foot member 1518 when the forces decrease so that less load is transferred between the primary foot member 1518 and the secondary foot member 1522.

The means for variably transferring energy can be associated with the primary elongated foot member 1518 and the secondary foot member 1522 to transfer energy between the primary elongated foot member and the secondary foot member. For example, the means for variably transferring energy can include variable resistance cell, indicated generally at 1532. The variable resistance cell 1532 can include a chamber 1568 disposed on a lower surface 1519 of the secondary foot member 1522. A piston 1564 can be coupled to the primary foot member 1518. The piston 1564 can have a piston rod 1561 that can extend through an aperture 1526 in the secondary foot member 1522 to a piston head 1562 that can be movable within a chamber 1568, such that the chamber and the piston can be displaceable with respect to one another between the first and second foot members.

Thus, the chamber 1568 can substantially enclose the piston head 1562, and the piston rod 1561 coupled to the piston head can extend out of the chamber and through the aperture 1526 in the secondary foot member 1522. An o-ring 1582 can form a seal between the rod and the chamber to prevent or reduce leakage of fluid from within the chamber.

The piston head 1562 inside the chamber 1568 can define a first variable space 1512 and a second variable space 1514 within the chamber. The first and second variable spaces 1512 and 1514 can be separated by the piston head 1562 such that the two spaces can be on opposite sides of the piston head. In this way, the volume of the spaces can vary or change as the piston head is moved within the chamber in response to the load factor.

At least one aperture or passage 1574 can be formed between the piston head 1562 and the chamber 1568. In one aspect, the aperture 1574 can be formed between the piston head 1562 and a wall 1566 of the chamber 1568. The aperture 1574 can include a channel formed in one of the piston head 1562 or wall 1566 of the chamber and a mating surface in the other of the piston head or wall of the chamber. Advantageously, the aperture 1574 formed between the piston head 1562 and a wall 1566 of the chamber 1568 can allow fluid to flow within the chamber 1568 between spaces 1512 and 1514 positioned on opposite sides of the piston head 1562, as indicated by the arrow at 1516.

As described in the embodiments above, a variable viscosity fluid 1012 can be disposed in the chamber 1568 and can be displaceable between the two spaces 1512 and 1514 through the aperture 1574 between the piston 1564 and the chamber 1568 in response to the load factor. The variable viscosity fluid 1012 can have a viscosity that is variable corresponding to the load factor to vary an ability of the variable viscosity fluid to flow through the at least one aperture. The piston 1564 can be movable in the chamber 1568 between a first position in response to a relatively larger load in which a lesser amount of the fluid passes through the aperture 1574, and a second position in response to a relatively smaller load in which a greater amount of fluid passes through the aperture 1574 into the second space 1514. The variable viscosity fluid 1012 can include a magneto rheologic fluid responsive to a magnetic field, an electro rheologic fluid responsive to an electric field, or combinations of magneto and electro rheologic fluids as well as shear stiffening materials that increase in viscosity with an increase in the load factor applied to the shear stiffening material.

The cell 1532 can also include a transducer 1578 to sense a load factor, and a power source (not shown), coupled to the transducer to power the variable viscosity fluid 1012. Control electronics (not shown) can be coupled to the transducer 1578 and the variable viscosity fluid 1012 in order to apply an electric or magnetic field in response to the load factor sensed by the transducer. The control electronics can be programmable, and the power source can include a generator.

It is to be understood that the above-referenced arrangements are only illustrative of the application for the principles of the present invention. Numerous modifications and alternative arrangements can be devised without departing from the spirit and scope of the present invention while the present invention has been shown in the drawings and fully described above with particularity and detail in connection with what is presently deemed to be the most practical and preferred embodiments(s) of the invention, it will be apparent to those of ordinary skill in the art that numerous modifications can be made without departing from the principles and concepts of the invention as set forth in the claims.

What is claimed:

1. A prosthetic foot device configured to provide a variable resistance in response to a load factor, the device comprising:
    a) first and second foot members, configured to be coupled to an amputee, the first foot member including:
        an upper forefoot member having an attachment section configured to be coupled to a socket, and extending downwardly therefrom; and
        a lower heel member having a heel section disposed at a natural location of a heel of a user, and an attachment section attached to the upper forefoot member; and
        the second foot member including a forefoot reinforcement member, disposed above the upper forefoot member;
    b) at least one of the first and second foot members being a resilient member capable of storing energy during deflection;
    c) a chamber, associated with one of the first and second foot members;
    d) a piston, associated with another of the first and second foot members and movable in the chamber, the piston and chamber defining a volume that changes in response to the load factor;

e) at least one passage, formed between a piston head of the piston and a wall of the chamber, and in communication with the chamber;

f) a variable viscosity fluid, disposed in the chamber and displaceable through the at least one passage between the piston head and the wall of the chamber in response to the load factor; and g) the variable viscosity fluid having a viscosity that is variable corresponding to the load factor to vary an ability of the variable viscosity fluid to flow through the at least one passage.

2. A device in accordance with claim 1, wherein the at least one passage includes a channel formed in one of the piston head or wall of the chamber and a mating side in the other of the piston head or wall of the chamber.

3. A device in accordance with claim 1, wherein the at least one passage formed between a head of the piston and a wall of the chamber allows fluid to flow within the chamber between opposite sides of the piston head.

4. A device in accordance with claim 1, wherein the variable viscosity fluid includes a shear stiffening material that increases in viscosity with an increase in the load factor applied to the shear stiffening material.

5. A device in accordance with claim 1, wherein the variable viscosity fluid includes at least one fluid selected from the group consisting of: a magneto rheologic fluid responsive to a magnetic field, or an electro rheologic fluid responsive to an electric field.

6. A device in accordance with claim 1, wherein the load factor includes at least one load factor selected from the group consisting of: a load, a load rate, a load acceleration, a strain, a strain rate, a strain acceleration, a pressure, a pressure rate, a pressure acceleration, a deflection, a deflection rate, and a deflection acceleration.

7. A device in accordance with claim 6, further comprising:
a transducer to sense a load factor;
a power source, coupled to the transducer;
control electronics, coupled to the transducer and the variable viscosity fluid, to apply an electric or magnetic field in response to the load factor sensed by the transducer.

8. A device in accordance with claim 1, wherein the variable viscosity fluid remains between the first and second foot members.

9. A device in accordance with claim 1, wherein the chamber and the piston are displaceable with respect to one another between the first and second foot members.

10. A prosthetic foot device with variable stiffness response, the device comprising:

a) a forefoot member having an attachment section configured to be coupled to a socket of an amputee, and extending downwardly therefrom configured to contact the ground during use;

b) a forefoot reinforcement member, disposed above the forefoot member;

c) the forefoot member and the forefoot reinforcement member being resilient members capable of storing energy during deflection;

d) a chamber, associated with one of the forefoot and forefoot reinforcement members;

e) a piston, associated with another of the forefoot and forefoot reinforcement members and movable in the chamber;

f) at least one passage formed between a head of the piston and a wall of the chamber to allow fluid communication within the chamber between opposite sides of the piston head;

g) a variable viscosity fluid, disposed in the chamber and displaceable through the at least one passage between the piston head and the wall of the chamber; and h) the variable viscosity fluid having a viscosity that is variable corresponding to a load factor to vary an ability of the variable viscosity fluid to flow through the at least one passage.

11. A device in accordance with claim 10, wherein the at least one passage includes a channel formed in one of the piston head or wall of the chamber and a mating side in the other of the piston head or wall of the chamber.

12. A device in accordance with claim 10, wherein the variable viscosity fluid includes a shear stiffening material that increases in viscosity with an increase in the load factor applied to the shear stiffening material.

13. A device in accordance with claim 10, wherein the variable viscosity fluid includes at least one fluid selected from the group consisting of: a magneto rheologic fluid responsive to a magnetic field, or an electro rheologic fluid responsive to an electric field.

14. A device in accordance with claim 13, further comprising:
a transducer to sense a load factor;
a power source, coupled to the transducer;
control electronics, coupled to the transducer and the variable viscosity fluid, to apply an electric or magnetic field in response to the load factor sensed by the transducer.

15. A prosthetic foot device configured to provide a variable resistance in response to a load factor, the device comprising:

a) first and second foot members, at least one of the foot members having an attachment end configured to be coupled to an amputee, and an opposite end, the first foot member including:
an upper forefoot member having an attachment section configured to be coupled to a socket, and extending downwardly therefrom; and
a lower heel member having a heel section disposed at a natural location of a heel of a user, and an attachment section attached to the upper forefoot member; and
the second foot member including a heel reinforcement member, disposed above the lower heel member;

b) at least one of the first and second foot members being a resilient member capable of storing energy during deflection;

c) a chamber, associated with one of the first and second foot members;

d) a piston, associated with another of the first and second foot members and movable in the chamber, the piston and chamber defining a volume that changes in response to the load factor;

e) at least one of the piston and the chamber being located closer to the opposite end of the at least one of the foot members than to the attachment end;

f) at least one passage, formed between a piston head of the piston and a wall of the chamber;

g) a variable viscosity fluid, disposed in the chamber and displaceable through the at least one passage in the piston in response to the load factor; and h) the variable viscosity fluid having a viscosity that is variable corresponding to the load factor to vary an ability of the variable viscosity fluid to flow through the at least one passage.

16. A device in accordance with claim 15, wherein the load factor includes at least one load factor selected from the group consisting of: a load, a load rate, a load acceleration, a strain, a strain rate, a strain acceleration, a pressure, a pressure rate, a pressure acceleration, a deflection, a deflection rate, and a deflection acceleration.

17. A device in accordance with claim 15, wherein the variable viscosity fluid includes a shear stiffening material that increases in viscosity with an increase in the load factor applied to the shear stiffening material.

18. A device in accordance with claim 15, wherein the variable viscosity fluid includes at least one fluid selected from the group consisting of: a magneto rheologic fluid responsive to a magnetic field, or an electro rheologic fluid responsive to an electric field.

19. A device in accordance with claim 18, further comprising:

a transducer to sense a load factor;

a power source, coupled to the transducer;

control electronics, coupled to the transducer and the variable viscosity fluid, to apply an electric or magnetic field in response to the load factor sensed by the transducer.

20. A device in accordance with claim 15, wherein the variable viscosity fluid remains between the first and second foot members.

21. A device in accordance with claim 15, wherein the chamber and the piston are displaceable with respect to one another between the first and second foot members.

* * * * *